US010544097B2

United States Patent
Srinivasan et al.

(10) Patent No.: US 10,544,097 B2
(45) Date of Patent: Jan. 28, 2020

(54) SOLID STATE FORMS OF N-[2-[(1S)-1-(3-ETHOXY-4-METHOXYPHENYL)-2-(METHYLSULFONYL)ETHYL]-2,3-DIHYDRO-1,3-DIOXO-1H-ISOINDOL-4-YL]ACETAMIDE AND PROCESS FOR PREPARATION THEREOF

(71) Applicant: MSN LABORATORIES PRIVATE LIMITED, Hyderabad, Telangana (IN)

(72) Inventors: Thirumalai Rajan Srinivasan, Telangana (IN); Eswaraiah Sajja, Telangana (IN); Venkat Reddy Ghojala, Telangana (IN); Pradeep Rebelli, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 15/755,993

(22) PCT Filed: Aug. 26, 2016

(86) PCT No.: PCT/IN2016/000220
§ 371 (c)(1),
(2) Date: Feb. 27, 2018

(87) PCT Pub. No.: WO2017/033206
PCT Pub. Date: Mar. 2, 2017

(65) Prior Publication Data
US 2019/0023655 A1    Jan. 24, 2019

(30) Foreign Application Priority Data

| Aug. 27, 2015 | (IN) | ............................. 4513/CHE/2015 |
| Dec. 18, 2015 | (IN) | ............................. 6950/CHE/2015 |
| Feb. 17, 2016 | (IN) | ............................. 201641005461 |

(51) Int. Cl.
*C07D 209/48*    (2006.01)

(52) U.S. Cl.
CPC ........ *C07D 209/48* (2013.01); *C07B 2200/13* (2013.01)

(58) Field of Classification Search
USPC ......................................................... 548/478
See application file for complete search history.

(56) References Cited

U.S. PATENT DOCUMENTS

| 6,962,940 | B2 |   | 11/2005 | Muller et al. | |
| 7,893,101 | B2 |   | 2/2011  | Muller et al. | |
| 10,196,355 | B2 | * | 2/2019 | Kavuru | ................ C07D 209/48 |
| 2017/0057916 | A1 | * | 3/2017 | Fang | .................... C07D 209/50 |
| 2017/0362175 | A1 | * | 12/2017 | Kavuru | ................ C07D 209/48 |
| 2018/0230097 | A1 | * | 8/2018 | Sanphui | ................ C07C 315/04 |

FOREIGN PATENT DOCUMENTS

| WO | WO 2009/120167 | 10/2009 | |
| WO | WO-2016135755 A1 * | 9/2016 | ........... C07D 209/48 |

OTHER PUBLICATIONS

International Search Report issued in International patent application No. PCT/IN2016/000220, dated Jan. 5, 2017.

* cited by examiner

*Primary Examiner* — Samantha L Shterengarts
(74) *Attorney, Agent, or Firm* — IP Pundit LLC

(57) ABSTRACT

The present invention, relates to solid state forms of N-[2-[(1S)-1-(3-ethoxy-4-methoxyphenyl)-2-(methylsulfonyl) ethyl]-2,3-dihydro-1,3-dioxo-1H-isoindol-4-yl]acetamide represented by the following structural formula-1 and process for their preparation. The present invention also relates to an improved process for the preparation of N-[2-[(1S)-1-(3-ethoxy-4-methoxyphenyl)-2-(methylsulfonyl)ethyl]-2, 3-dihydro-1,3-dioxo-1H-isoindol-4-yl]acetamide compound of formula-1 and intermediates thereof.

Formula-1

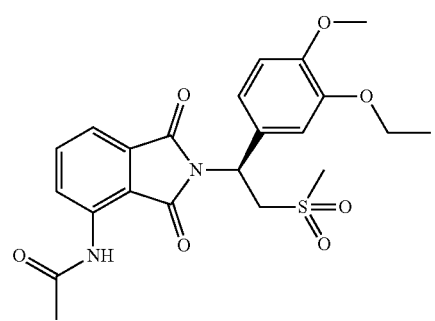

6 Claims, 5 Drawing Sheets

SOLID STATE FORMS OF N-[2-[(1S)-1-(3-ETHOXY-4-METHOXYPHENYL)-2-(METHYLSULFONYL)ETHYL]-2,3-DIHYDRO-1,3-DIOXO-1H-ISOINDOL-4-YL]ACETAMIDE AND PROCESS FOR PREPARATION THEREOF

RELATED APPLICATIONS

This application is a national phase application under 35 U.S.C. § 371 of International Application No. PCT/IN2016/000220, filed on Aug. 26, 2016, which claims priority to Indian patent application 513/CHE/2015 filed on Aug. 27, 2015; 6950/CHE/2015 filed on Dec. 18, 2015; and 201641005461 filed on Feb. 17, 2016; the disclosures of all of which are incorporated herein by reference in their entirety.

Field of the Invention

The present invention provides solid state forms of N-[2-[(1S)-1-(3-ethoxy-4-methoxyphenyl)-2-(methylsulfonyl)ethyl]-2,3-dihydro-1,3-dioxo-1H-isoindol-4-yl]acetamide represented by the following structural formula-1 and process for their preparation.

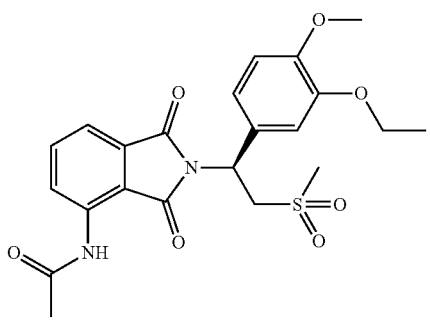

Formula-1

The present invention also provides an improved process for the preparation of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1 and intermediates thereof.

BACKGROUND OF THE INVENTION

N-[2-[(S)-1-(3-ethoxy-4-methoxyphenyl)-2-(methylsulfonyl)ethyl]-2,3-dihydro-1,3-dioxo-1H-isoindol-4-yl]acetamide commonly known as Apremilast is a phosphodiesterase 4 (PDE4) inhibitor. Apremilast was approved by the USFDA for the treatment of adults with active psoriatic arthritis.

U.S. Pat. No. 7,427,638B2 specifically describes Apremilast, its related compounds and process for their preparation.

U.S. Pat. No. 7,893,101B2 describes seven crystalline polymorphic forms of Apremilast namely form-A, form-B, form-C, form-D, form-E, form-F and form-G and also described process for their preparation.

U.S. Pat. No. 7,893,101B2 patent also describes mixture of crystalline form-A, form-B, form-C, form-D, form-E, form-F, form-G of Apremilast with amorphous form.

Since the development of new polymorphic forms of an active pharmaceutical ingredient provides new opportunity to improve the performance characteristics of pharmaceutical finished product, the development of new polymorphic forms is always encouraged.

Furthermore, solid state study of an active pharmaceutical ingredient aims to widen the variety of crystalline forms that a formulation scientist has available for designing a pharmaceutical dosage form with desired characteristics.

The present inventors surprisingly found novel crystalline polymorph of N-[2-[(1S)-1-(3-ethoxy-4-methoxyphenyl)-2-(methylsulfonyl)ethyl]-2,3-dihydro-1,3-dioxo-1H-isoindol-4-yl]acetamide having advantageous properties which is useful and well suitable for the preparation of various pharmaceutical compositions.

The present inventors also developed improved process for the preparation of N-[2-[(1S)-1-(3-ethoxy-4-methoxyphenyl)-2-(methylsulfonyl)-2-(met)ethyl]-2,3-dihydro-1,3-dioxo-H-isoindol-4-yl]acetamide compound of formula-1 and intermediates thereof.

BRIEF DESCRIPTION OF THE INVENTION

The first aspect of the present invention is to provide a novel crystalline polymorph of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1, herein after designated as crystalline form-M.

The second aspect of the present invention is to provide a process for the preparation of novel crystalline form-M of compound of formula-1.

The third aspect of the present invention is to provide amorphous form of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1.

The fourth aspect of the present invention is to provide a process for the preparation of amorphous form of compound of formula-1.

The fifth aspect of the present invention is to provide a process for the preparation of 1-(3-ethoxy-4-methoxyphenyl)-2-(methylsulfonyl)ethanamine compound of formula-4.

The sixth aspect of the present invention is to provide an improved process for the preparation of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1.

The seventh aspect of the present invention is to provide a process for the purification, of (S)-1-(3-ethoxy-4-methoxyphenyl)-2-(methylsulfonyl)ethanamine chiral amino acid-addition salt compound of general formula-5.

The eighth aspect of the present invention is to provide a process for the preparation of 3-aminophthalic acid compound of formula-11.

DETAILED DESCRIPTION OF THE INVENTION

Figure 1:
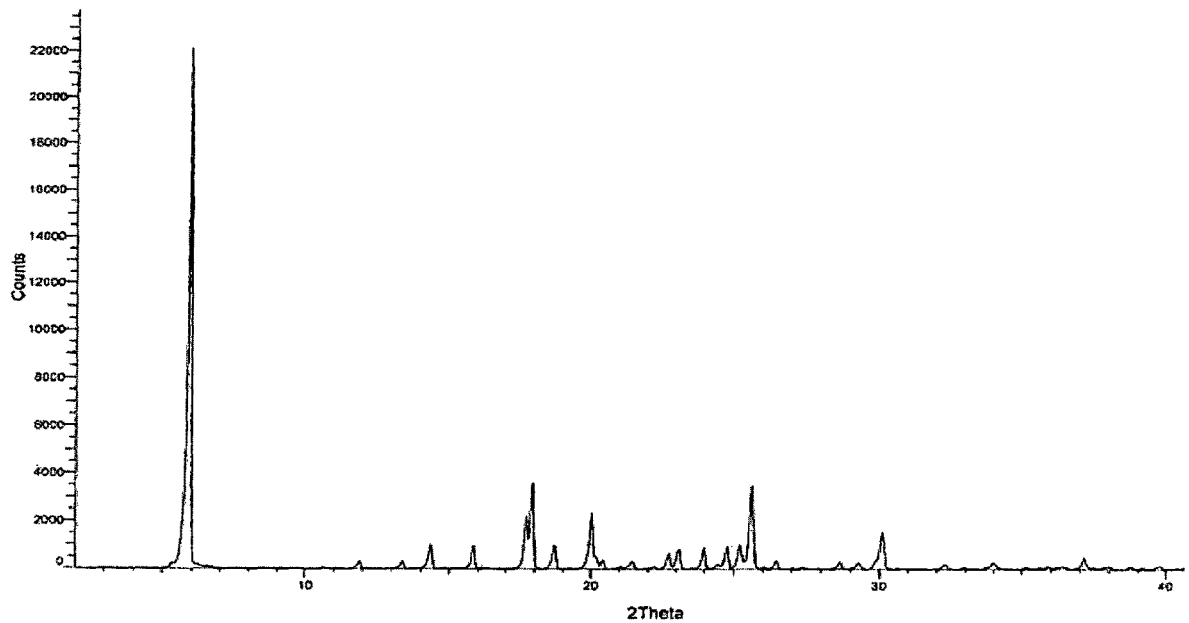
FIG. 1: Illustrates the PXRD pattern of 1-(3-ethoxy-4-methoxyphenyl)-2-(methylsulfonyl) ethanamine (Formula-4)
Figure 2:
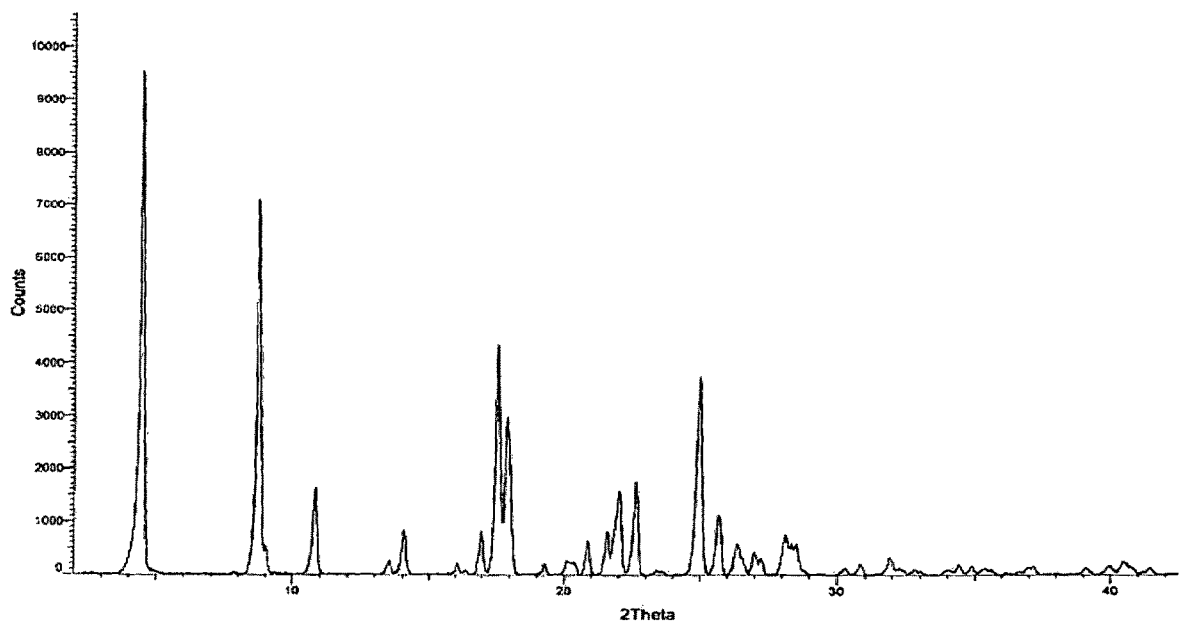
FIG. 2: Illustrates the PXRD pattern of (S)-1-(3-ethoxy-4-methoxyphenyl)-2-(methylsulfonyl)ethanamine N-acetyl-L-leucine salt (Formula-5a)
Figure 3:
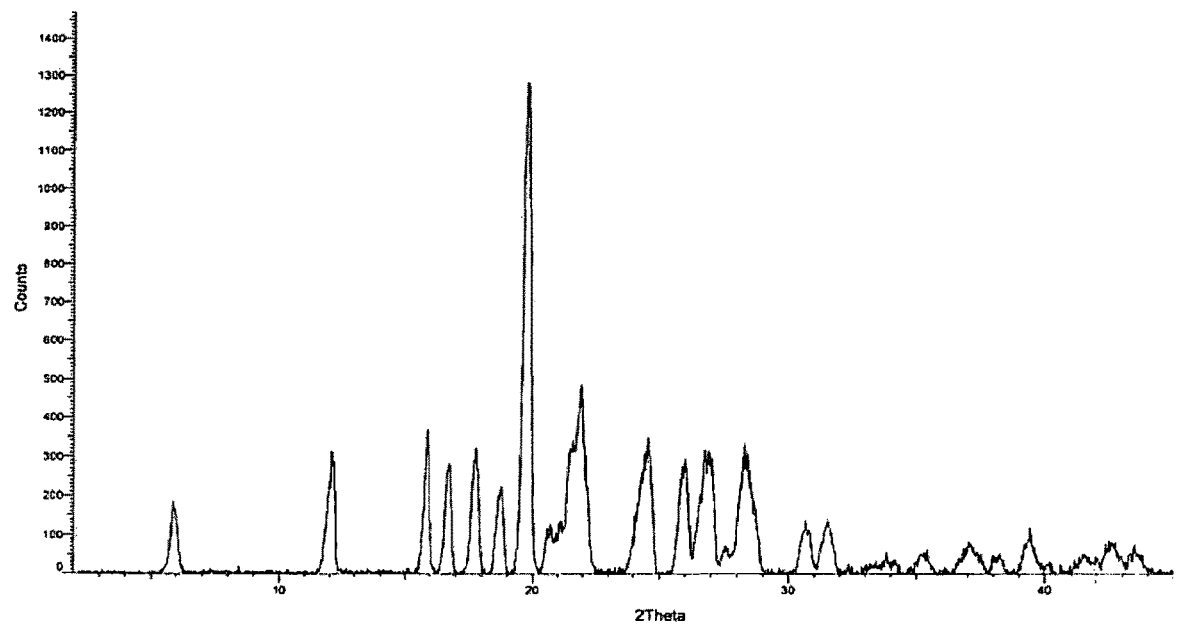
FIG. 3: Illustrates the PXRD pattern of (S)-1-(3-ethoxy-4-methoxyphenyl)-2-(methylsulfonyl)ethanamine (Formula-6)
Figure 4:
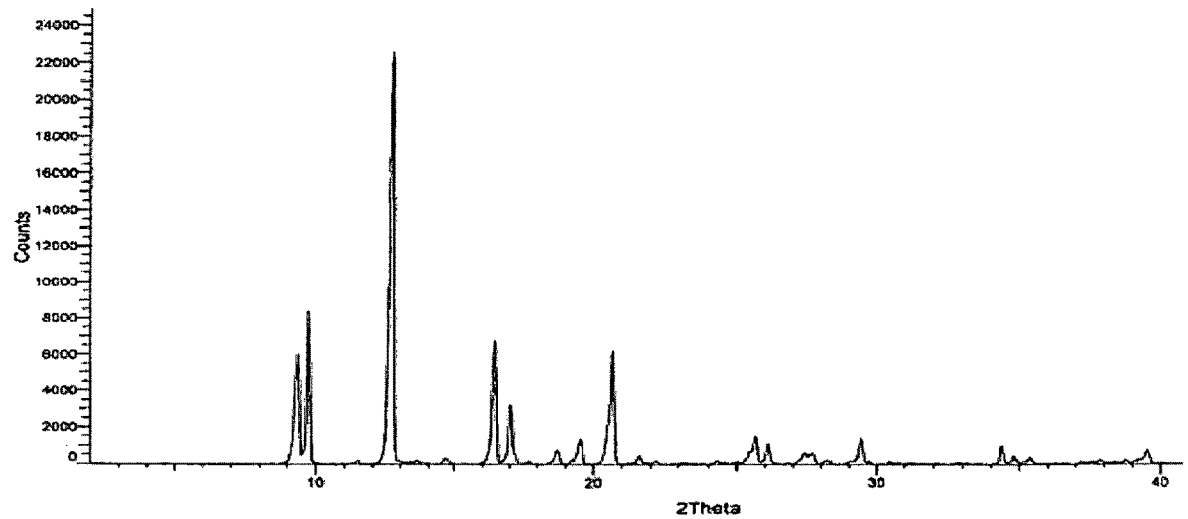
FIG. 4: Illustrates the PXRD pattern of N-(1,3-dioxo-1,3-dihydroisobenzofuran-4-yl) acetamide (Formula-7)

The term "suitable solvent" used in the present invention refers to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-prolyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, tert-butanol, ethane-1,2-diol, propane-1,2-diol and the like; "polar solvents" such as water; formic acid, acetic acid or mixture of any of the aforementioned solvents.

The term "suitable base" used in the present invention refers to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, lithium methoxide, lithium ethoxide, sodium tert.butoxide, potassium tert.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropyl amine, diisopropylethylamine, diisobutylamine, triethylamine, triisopropyl amine, tributylamine, tert.butyl amine, pyridine, 4-dimethylaminopyridine, imidazole, N-methylimidazole; 1,8-diazabicyclo[5.4.0]undec-7-ene (DBU), 1,5-diazabicyclo[4.3.0]non-5-ene (DBN), N-methylmorpholine; 1,4-diazabicyclo[2.2.2]octane (DABCO), 2,6-lutidine and the like; "organolithium bases" such as methyl lithium, n-butyl lithium, lithium diisopropylamide and the like; "organosilicon bases" such as lithium hexamethyldisilazide, sodium hexamethyldisilazide, potassium hexamethyldisilazide and the like or their mixtures.

The first aspect of the present invention provides a novel crystalline polymorph of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1. The novel crystalline polymorph of compound of formula-1 of the present invention is characterized by its PXRD pattern having peak at 5.4±0.20 of 2θ.

The novel crystalline polymorph of compound of formula-1 is further characterized by its PXRD pattern having peaks at 8.5 and 27.2±0.2° of 2θ.

Figure 5:
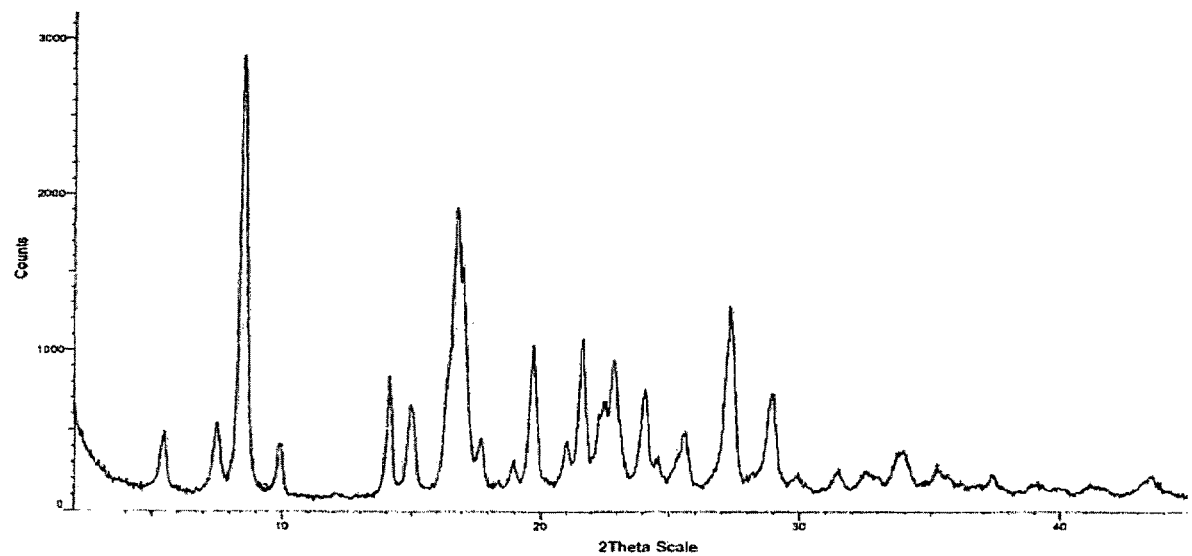
FIG. 5: Illustrates the PXRD pattern of crystalline form-M of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1.

In an another embodiment the said novel crystalline polymorph is further characterized by its PXRD pattern having peaks at 7.5, 9.9, 14.1, 14.9, 16.7, 16.9, 17.7, 19.7, 21.6, 22.5, 22.8, 24.0, 25.5 and 28.9±0.2° of 2θ and the PXRD pattern as shown in FIG. 5.

The novel crystalline polymorph of compound of formula-1 of the present invention is herein after designated as crystalline form-M.

The crystalline form-M of compound of formula-1 of the present invention is non-hygroscopic in nature which is highly advantageous for the formulators.

The crystalline form-M of the present invention is stable at various conditions viz.,
a) Stress (10 ton pressure, 3 min)
b) UV light (254 nm, 24 hrs)
c) Thermal (60° C., 24 hrs)
d) Hygroscopicity (75% RH, 24 hrs))

The above data proves that crystalline form-M of compound of formula-1 is highly stable which is desirable for formulation scientist to prepare finished-drug product.

The second aspect of the present invention provides a process for the preparation of crystalline form-M of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1, comprising of;
a) Dissolving the compound of formula-1 in a suitable first solvent,
b) optionally filtering the solution,
c) combining the solution with a suitable second solvent,
d) filtering the precipitated solid and drying to provide crystalline form-M of compound of formula-1.

Wherein, in step-a) the suitable first solvent is selected from ketone solvents; and the dissolution of compound of formula-1 in a suitable first solvent is carried out at a suitable temperature ranges between 10° C. to reflux temperature of the solvent used.

In step-c) the suitable second solvent is selected from polar solvents; and combining the solution of step-a) with a suitable second solvent is carried out at a suitable temperature ranges from 0° C. to reflux temperature of the solvent used.

Compound of formula-1 which is used as input in the above process for the preparation of crystalline form-M of compound of formula-1 can be prepared by any of the known processes or it can be prepared by the process as described in the present application.

The crystalline form-M of compound of formula-1 can be utilized as input for the preparation of any of the known polymorphic forms and it can also be used as input for the preparation of novel crystalline polymorphs of compound of formula-1.

A preferred embodiment of the present invention provides a process for the preparation of crystalline form-M of compound of formula-1, comprising of;

a) Dissolving the compound of formula-1 in acetone,
b) optionally filtering the solution,
c) combining the solution with water,
d) filtering the precipitated solid and drying to provide crystalline form-M of compound of formula-1.

A more preferred embodiment of the present invention provides a process for the preparation of crystalline form-M of compound of formula-1, comprising of;
a) Dissolving the compound of formula-1 in acetone,
b) optionally filtering the solution,
c) slowly adding the solution to pre-cooled water at 5-10° C.,
d) filtering the precipitated solid and drying to provide crystalline form-M of compound of formula-1.

The third aspect of the present invention provides amorphous form of N-[2-[(1S)-1-(3-ethoxy-4-methoxyphenyl)-2-(methylsulfonyl)ethyl]-2,3-dihydro-1,3-dioxo-1H-isoindol-4-yl]acetamide compound of formula-1.

The amorphous form of compound of formula-1 is prepared by the process as illustrated in the present invention and it is useful and well suitable for the preparation of various pharmaceutical compositions formulated in a manner suitable for the route of administration to be used where at least a portion of compound of formula-1 is present in the composition in particular polymorphic form mentioned. Such pharmaceutical compositions may comprise compound of formula-1 present in the composition in a range of between 0.005% and 100% (wt/wt), with the balance of the pharmaceutical composition comprising additional substances such as excipients, diluents, lubricants, binders, wetting agents, disintegrating agents, glidants, sweetening agents, flavoring agents, emulsifying agents, solubilizing agents, pH buffering agents, perfuming agents, surface stabilizing agents, suspending agents and other conventional pharmaceutically inactive agents.

The fourth aspect of the present invention provides process for the preparation of amorphous form of compound of formula-1, comprising of;
a) Dissolving the compound of formula-1 in a suitable solvent;
b) removing the solvent from the reaction mixture to provide amorphous form of compound of formula-1.

Wherein, in step-a) the suitable solvent is selected from ketone solvents, chloro solvents, ester solvents, ether solvents, nitrile solvents, polar-aprotic solvents or their mixtures; and the dissolution of compound of formula-1 in any of the above described solvents can be done at a suitable temperature generally ranges between 20° C. to reflux temperature of the solvent used.

In step-b) removal of solvent from the reaction mixture is carried out by various techniques including but not limited to evaporation, evaporation under reduced pressure, flash evaporation, vacuum drying, concentrating the reaction mixture, atmospheric distillation, vacuum distillation, distillation by using a rotational distillation device such as a Buchi Rotavapor, agitated thin film drying, melt extrusion, spray drying, freeze drying (lyophilization), spray-freeze drying, addition of suitable anti-solvent to the reaction mixture followed by filtration of the precipitated solid, cooling the clear solution to lower temperatures to precipitate the solid followed by filtration of the reaction or by any other suitable techniques known in the art.

A preferred embodiment of the present invention provides a process for the preparation of amorphous form of compound of formula-1, comprising of;

a) Dissolving the compound of formula-1 in a suitable nitrile solvent,
b) optionally filtering the solution,
c) combining the solution with water,
d) filtering the precipitated solid to provide amorphous form of compound of formula-1.

Another preferred embodiment of the present invention provides a process for the preparation of amorphous form of compound of formula-1, comprising of;
a) Dissolving the compound of formula-1 in 1,4-dioxane,
b) optionally filtering the solution,
c) combining the solution with a suitable anti-solvent,
d) filtering the precipitated solid to provide amorphous form of compound of formula-1.

Wherein, in step-c) the suitable anti-solvent is selected from water, hydrocarbon solvents or their mixtures.

A more preferred embodiment of the present invention provides a process for the preparation of amorphous form of compound of formula-1, comprising of;
a) Dissolving the compound of formula-1 in 1,4-dioxane,
b) optionally filtering the solution,
c) combining the solution with water,
d) filtering the precipitated solid to provide amorphous form of compound of formula-1.

U.S. Pat. No. 8,242,310B2 assigned to Celgene, has described the process for the preparation of 1-(3-ethoxy-4-methoxyphenyl)-2-(methylsulfonyl)ethanamine compound of formula-4, by reacting 3-ethoxy-4-methoxybenzonitrile compound of formula-2 with Lithiated dimethylsulfone followed by reducing the resulting intermediate to provide compound of formula-4.

In the above described process, Lithiated dimethylsulfone is prepared by reacting dimethylsulfone with n-BuLi in presence of a solvent.

Organolithium compounds are highly reactive species and require specialized handling techniques. They are often corrosive, flammable and sometimes pyrophoric in nature. Alkyl lithium reagents can also undergo thermal decomposition to form the corresponding alkyl species and lithium hydride. Organolithium reagents are typically stored below 10° C. and reactions are conducted using air free techniques. Organolithium reagents react with ethers, which are often used as solvents.

In particular, n-BuLi is highly reactive species and highly pyrophoric in nature. Its usage has many disadvantages particularly on commercial scale in safety point of view. Hence, in view of all the above concerns usage of n-BuLi is not advisable on commercial scale.

Hence, there is a significant need to develop alternate process for the preparation of compound of formula-4 from compound of formula-2 by using safer reagents.

The present inventors earnestly tried to develop alternate process. After numerous trails the present inventors found that the usage of Grignard reagent for the above step has many advantages. The advantages include Grignard reagents are cheaper, easy to handle; non-pyrophoric and industrially viable.

The reaction of compound of formula-2 with dimethyl sulfone in presence of Grignard reagent has provided the product with excellent quality and higher yields. Hence, the present invention is highly advantageous.

An embodiment of the present invention provides a process for the preparation of 1-(3-ethoxy-4-methoxyphenyl)-2-(methylsulfonyl)ethanamine compound of formula-4, comprising of reacting the 3-ethoxy-4-methoxybenzonitrile compound of formula-2 with dimethylsulfone in presence of Grignard reagent.

The fifth aspect of the present invention provides a process for the preparation of 1-(3-ethoxy-4-methoxyphenyl)-2-(methylsulfonyl)ethanamine compound of formula-4, comprising of reacting the 3-ethoxy-4-methoxybenzonitrile compound of formula-2 with dimethylsulfone in presence of Grignard reagent in a suitable solvent followed by reduction of the obtained compound with a suitable reducing agent in a suitable solvent to provide compound of formula-4.

Wherein, the "Grignard reagent" refers to substituted or unsubstituted alkyl/vinyl/aryl magnesium halides; preferably methyl magnesium chloride;

The suitable reducing agent is selected from NaBH(OAc)$_3$, alkali metal borohydrides, BF$_3$-etherate, LiAlH$_4$, Pd and the like; and the reduction reaction is carried out optionally in presence of an acid such as acetic acid, formic acid, methanesulfonic acid, trifluoroacetic acid, 4-(trifluoromethyl)benzoic acid, p-toluenesulfonic acid, hydrochloric acid, nitric acid, sulfuric acid, phosphoric acid or combination thereof;

The suitable solvent is independently selected from hydrocarbon solvents, ether solvents, ester solvents, polar-aprotic solvents, chloro solvents, ketone solvents, nitrile solvents, alcohol solvents, polar solvents, formic acid, acetic acid or their mixture.

In the above process, the amount of Grignard reagent used is ranges from 1.0-50 mole ratio, preferably from 2.0-4.0 mole ratio per one mole of compound of formula-2. The reaction of 3-ethoxy-4-methoxybenzonitrile compound of formula-2 with dimethylsulfone can also be carried out in presence of a suitable base described above.

The sixth aspect of the present invention provides an improved process for the preparation of N-[2-[(S)-1-(3-ethoxy-4-methoxyphenyl)-2-(methylsulfonyl)ethyl]-2,3-dihydro-1,3-dioxo-1H-isoindol-4-yl]acetamide compound of formula-1, comprising of; a) Reacting the 3-ethoxy-4-methoxybenzonitrile compound of formula-2

Formula-2

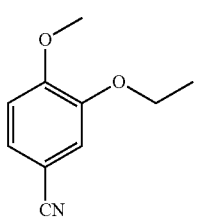

with dimethylsulfone in presence of Grignard reagent in a suitable solvent to provide (E)-1-(3-ethoxy-4-methoxyphenyl)-2-(methylsulfonyl)ethenamine compound of formula-3, Formula-3

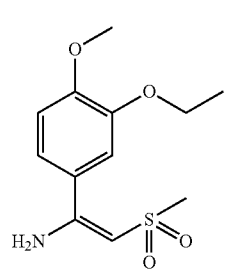

b) reducing the compound of formula-3 with a suitable reducing agent in a suitable solvent to provide 1-(3-ethoxy-4-methoxyphenyl)-2-(methylsulfonyl)ethanamine compound of formula-4, Formula-4

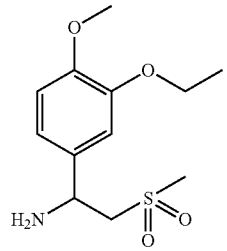

c) resolution of compound of formula-4 by treating it with a suitable chiral amino acid in a suitable solvent or mixture of solvents to provide chiral amino acid-addition salt compound of general formula-5, Formula-5

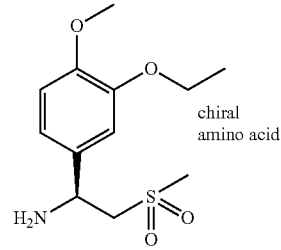

d) treating the compound of general formula-5 with a suitable base in a suitable solvent or mixture of solvents to provide (S)-1-(3-ethoxy-4-methoxyphenyl)-2-(methylsulfonyl)ethanamine compound of formula-6, Formula-6

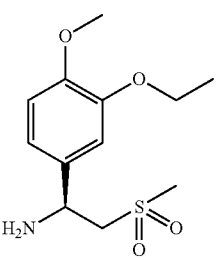

e) treating the compound of formula-6 with a suitable chiral amino acid in a suitable solvent or mixture of solvents to provide chiral amino acid-addition salt compound of general formula-5, f) reacting the compound of general formula-5 with N-(1,3-dioxo-1,3-dihydroisobenzofuran-4-yl)acetamide compound of formula-7

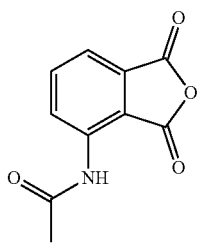

Formula-7 in a suitable solvent to provide compound of formula-1,
g) purifying the compound of formula-1 from a suitable solvent or mixture of solvents to provide pure compound of formula-1.

Wherein, in step-a) the term "Grignard reagent" refers to substituted or unsubstituted alkyl/vinyl/aryl magnesium halides; preferably methyl magnesium chloride;
in step-b) the suitable reducing agent is selected from but not limited to NaBH(OAc)$_3$, alkali metal borohydrides, BF$_3$-etherate, LiAlH$_4$, Pd and the like; and the reduction reaction is carried out optionally in presence of an acid such as acetic acid, formic acid, methanesulfonic acid, trifluoroacetic acid, 4-(trifluoromethyl)benzoic acid, p-toluenesulfonic acid, hydrochloric acid, nitric acid, sulfuric acid, phosphoric acid or combination thereof;
in step-c) & step-e) the suitable chiral amino acid is independently selected from but not limited to L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2 amino isobutyric acid, 3-amino propionic acid, norleucine, norvaline, hydroxyproline, sarcosine, citrulline, cysteic acid, t-butylglycine, t-butylalanine, phenylglycine, cyclohexylalanine, N-acetyl-leucine and the like;
in step-d) the suitable base is selected from but not limited to inorganic bases, organic bases or their mixtures;
in step-a) to step-g) the suitable solvent wherever necessary is independently selected from but not limited to hydrocarbon solvents, ether solvents, ester solvents, polar-aprotic solvents, chloro solvents, ketone solvents, nitrile solvents, alcohol solvents, polar solvents, formic acid, acetic acid or their mixtures.

In the above process, the compound of formula-2 can be procured from any commercial sources or it can be prepared by any of the processes known in the art.

The compound of formula-7 utilized in step-f) Of the above aspect can be procured from any of the commercial sources or it can be synthesized by any of the processes known in the art or it can be synthesized by the process of the present invention.

The compound of formula-4 of the present invention can also be prepared by the processes as described in scheme-IV of the present invention.

The compound of formula-4 of the present invention is useful for the preparation of compound of formula-5 as well as compound of formula-1.

The seventh aspect of the present invention provides a process for the purification of (S)-1-(3-ethoxy-4-methoxyphenyl)-2-(methylsulfonyl)ethanamine chiral amino acid addition salt compound of general formula-5, comprising of;

a) treating the compound of general formula-5 with a suitable base in a suitable solvent or mixture of solvents to provide compound of formula-6,
b) treating the compound of formula-6 with a suitable chiral amino acid in a suitable solvent or mixture of solvents to provide pure compound of general formula-5.

Wherein, in step-a) the suitable base is same as defined in step-d) of the sixth aspect of the present invention;
in step-b) the suitable chiral amino acid is same as defined in step-c) of the sixth aspect of the present invention;
in step-a) & step-b) the suitable solvent is same, as defined in sixth aspect of the present invention.

The above purification process for compound of general formula-5 can be optionally performed more than one time in order to achieve compound of general formula-5 with enhanced chiral purity.

The present invention also provides crystalline polymorphs of various intermediate compounds of the present invention, which are useful for the preparation of pure compound of formula-1.

The compound of formula-1 can also be prepared by the processes as described in scheme-II of the present invention.

The eighth aspect of the present invention provides a process for the preparation of 3-aminophthalic acid compound of formula-11, comprising of reducing the 3-nitrophthalic acid compound of formula-8 with a suitable reducing agent in a suitable solvent to provide compound of formula-11.

The reduction of nitro group to amine in the present invention is carried out by using suitable reducing agent selected from but not limited to Pd, Pt, Raney Ni, hydrazine hydrate in combination with FeCl$_3$ or a metal catalyst such as Fe, Raney Ni and the like; Fe or Zn in combination with HCl; acetic acid, NH$_4$Cl and the like; Sn—HCl, SnCl$_2$ and the like. The reduction step is carried out optionally in presence of a suitable base. The base is selected from inorganic bases such as hydroxides, alkoxides, carbonates, bicarbonates of alkali metals.

A preferred embodiment of the present invention provides a process for the preparation of 3-aminophthalic acid compound of formula-11, comprising of reducing the 3-nitrophthalic acid compound of formula-8 with Fe-hydrazine hydrate optionally in presence of a suitable base in a suitable solvent to provide compound of formula-11.

The acetylation of compound of formula-10 or compound of formula-11 of the present invention can be done using acetyl chloride, acetic anhydride or acetic acid.

An embodiment of the present invention provides process for the preparation of crystalline form-B of compound of formula-1, comprising of;

a) Dissolving the compound of formula-1 in dichloromethane,
b) optionally filtering the solution,
c) removing the solvent from the solution,
d) adding methanol and ethyl acetate to the obtained compound,
e) heating the reaction mixture,
f) cooling the reaction mixture,
g) filtering the solid and drying to provide crystalline form-B of compound of formula-1.

Wherein, in step-c) the solvent is removed by distillation;
In step-e) the reaction mixture is heated to temperature ranges from 35° C. to 80° C.;
In step-f) the reaction mixture is cooled to temperature ranges from 30° C. to −30° C.

The PXRD analysis of compounds of the present invention was carried out using BRUKER/D8 ADVANCE X-Ray diffractometer using CuKα radiation of wavelength 1.5406 A° and at a continuous scan speed of 0.03°/min.

The compound of formula-1 of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling/micronization may be performed before drying or after drying of the product.

Compound of formula-1 produced by the present invention was analyzed by HPLC under the following conditions; Apparatus: A liquid chromatograph equipped with variable wavelength UV detector; Column: Kromasil 100 C18, 250×4.6 mm, 5 μm or equivalent; Column temperature: 30° C.; Wave length: 230 nm; Auto sampler temperature: 5° C.; Injection volume: 5 μL; Elution: Gradient; Diluent: Acetonitrile:Buffer (70:30 v/v); Buffer: Take 1.0 mL of orthophosphoric acid and 3 gm of 1-octane sulfonic acid anhydrous in 1000 mL of milli-Q-water and filter this solution through 0.22 μm Nylon membrane filter paper; Mobile phase-A: Buffer (100%); Mobile phase-B: Acetonitrile: Buffer (70:30 v/v).

Enantiomeric purity of compound of formula-1 produced by the present invention was analyzed by HPLC under the following conditions;
Apparatus: A liquid chromatograph equipped with variable wavelength UV detector; Column: CHIRAL PAK ID-3, 250×4.6 mm, 3 μm or equivalent; Column temperature: 30° C.; Wave length: 260 nm; Injection volume: 5 μL; Elution: Isocratic; Diluent: Acetonitrile; Mobile phase: Methyl tert-.butyl ether:Ethanol:Diethylamine (900:100:1.0 v/v/v).

The present invention is schematically represented as follows.

Scheme-I:

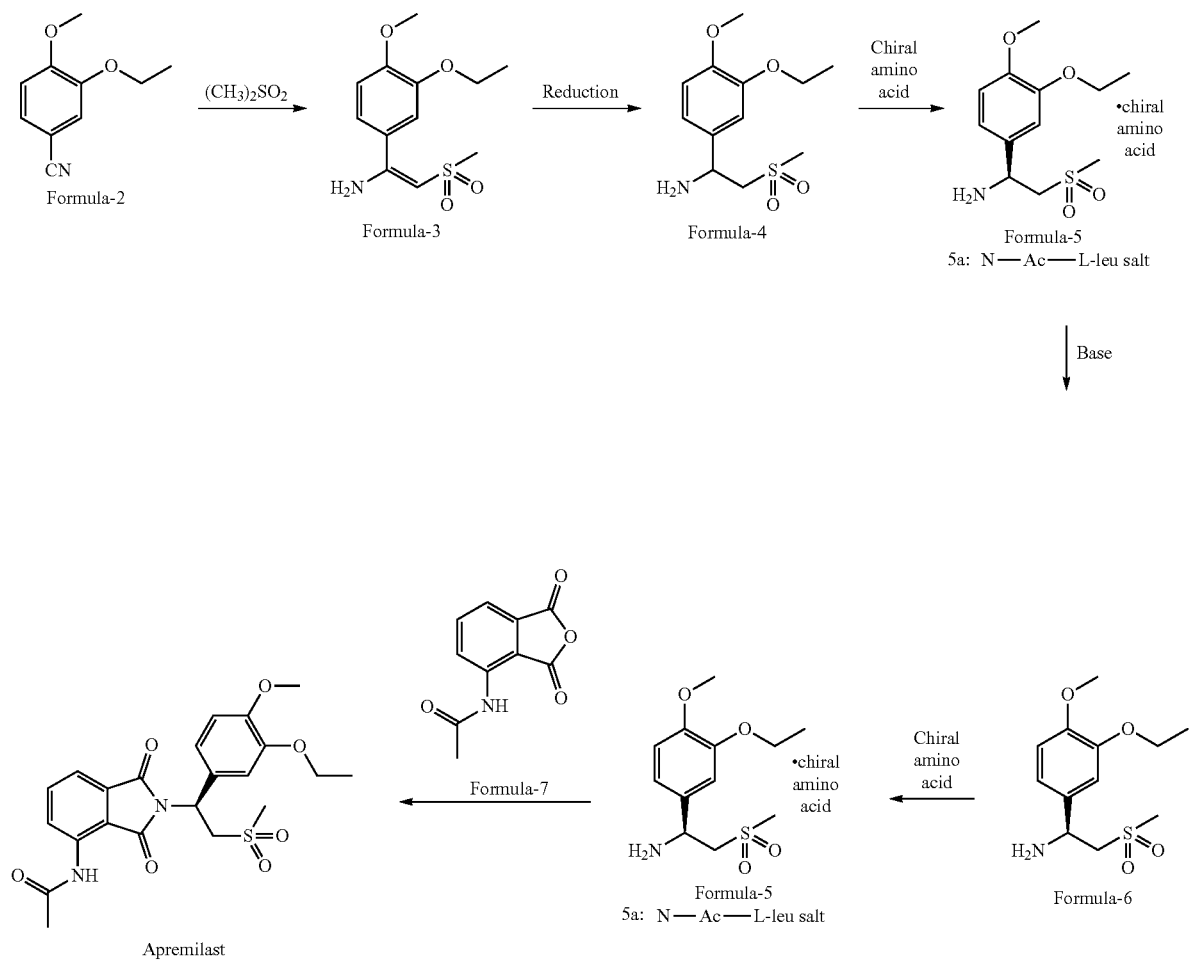

Scheme-II:
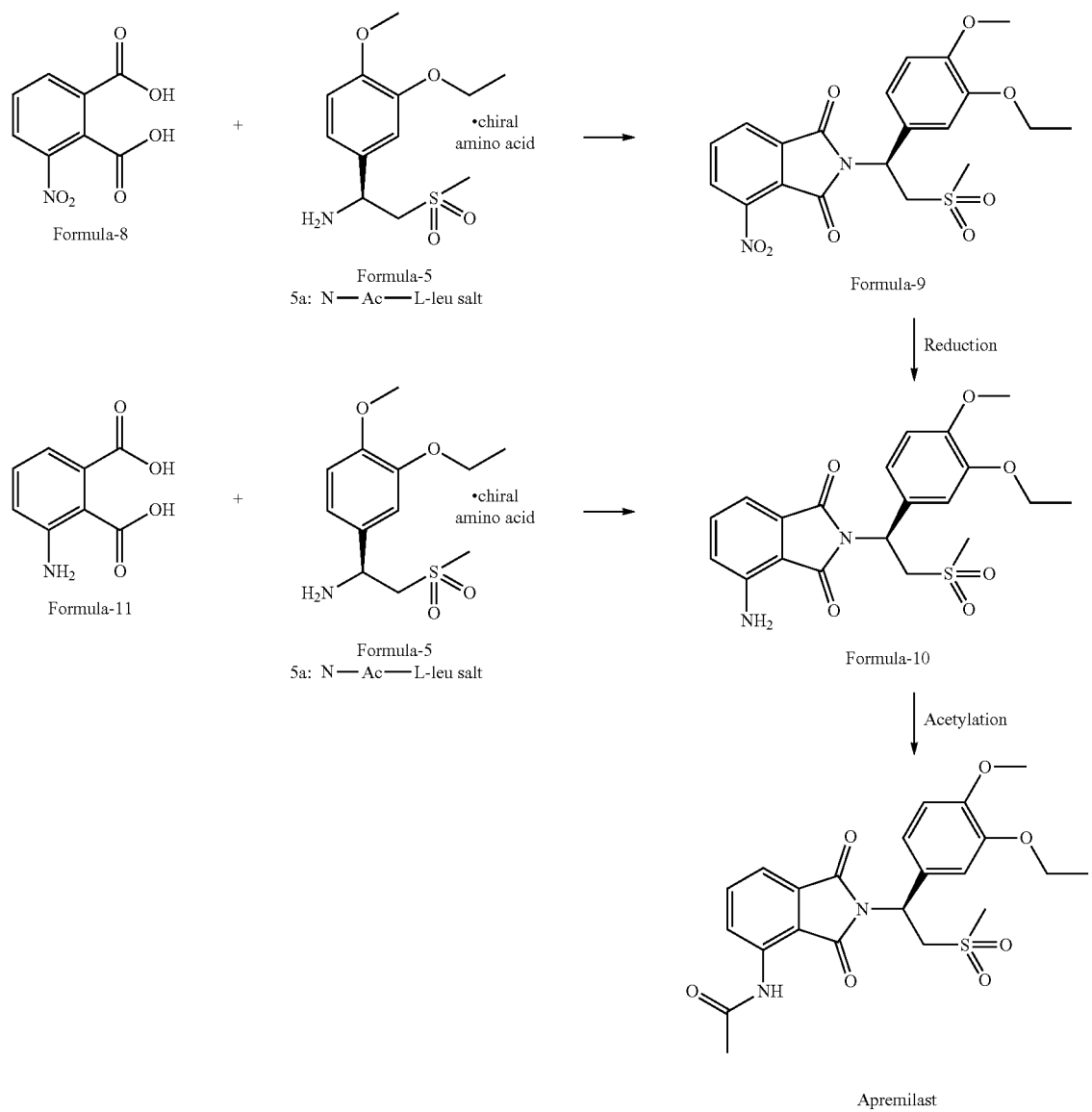
Scheme-III:
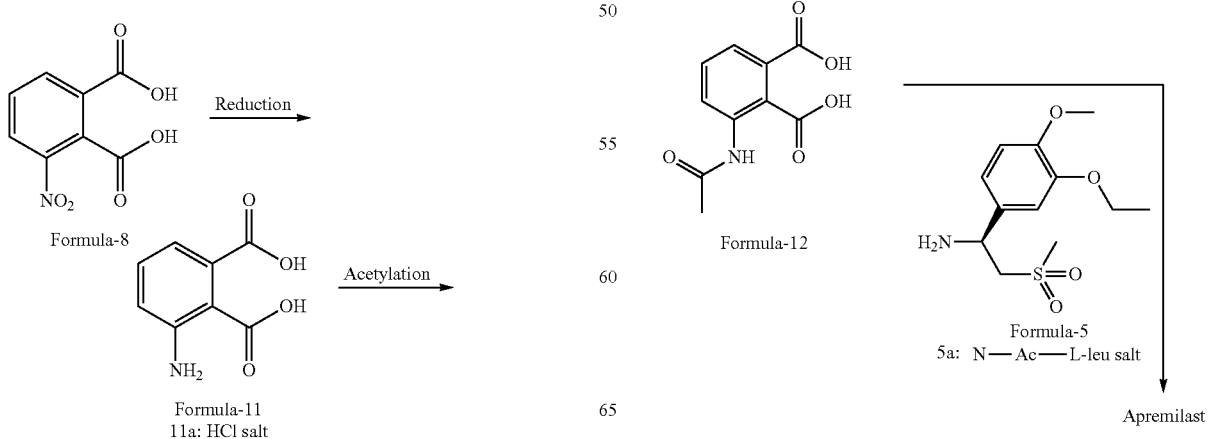

Scheme-IV:

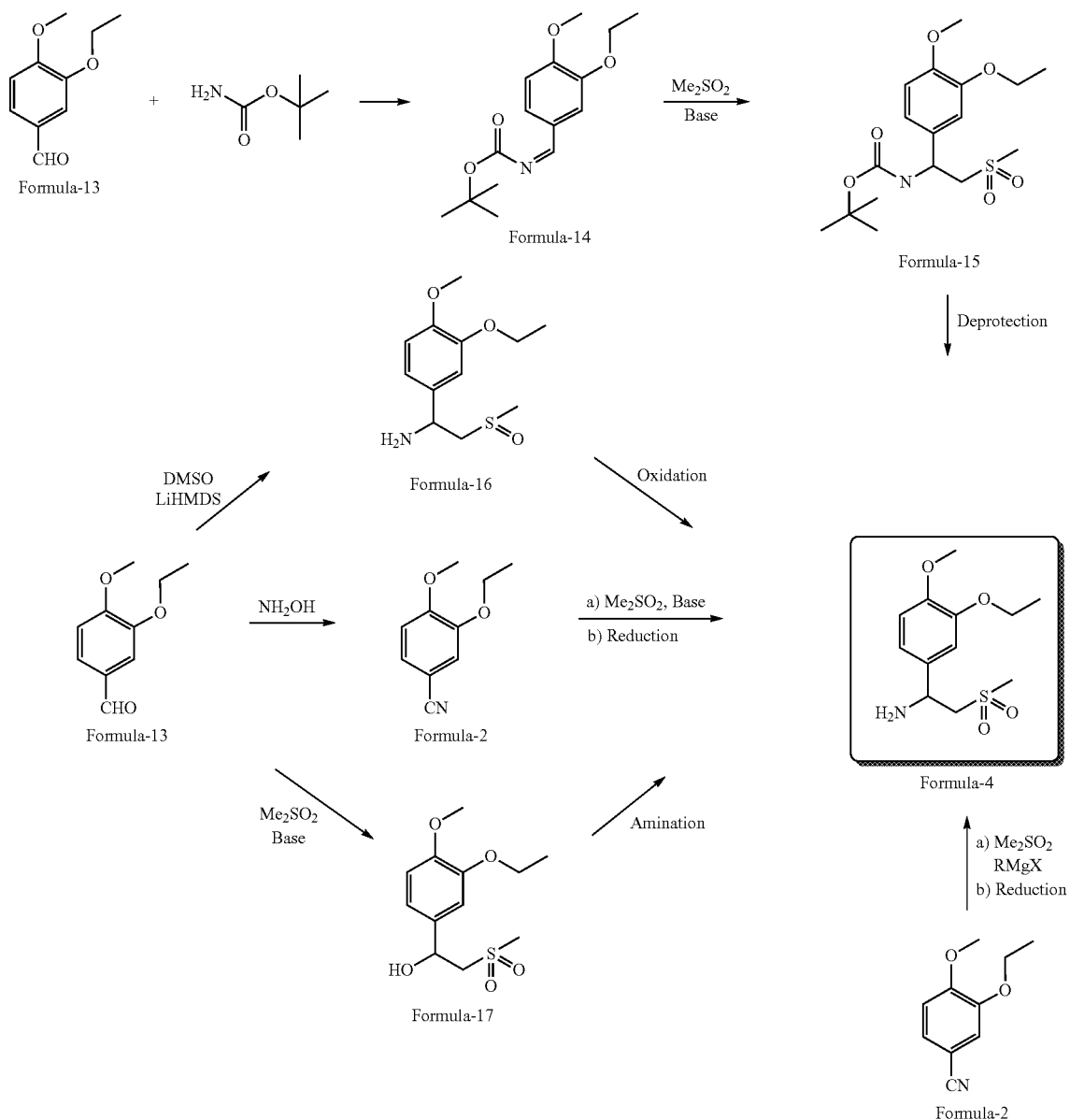

The best mode of carrying out the present invention is illustrated by the below mentioned examples. These examples are provided as illustration only and hence should not be construed as limitation to the scope of the invention.

EXAMPLES

Example-1: Preparation of 1-(3-ethoxy-4-methoxyphenyl)-2-(methylsulfonyl) ethanamine (Formula-4)

3M Methyl magnesium chloride solution in tetrahydrofuran (235.1 ml) was slowly added to a pre-cooled mixture of 3-ethoxy-4-methoxybenzonitrile compound of formula-2 (50 gm), dimethyl sulfone (53.1 gm) and tetrahydrofuran (250 ml) at 0-5° C. under nitrogen atmosphere. Raised the temperature of the reaction mixture to 25-30° C. and stirred for 6 hrs at the same temperature. Sodium borohydride (21.5 gm) was added to the reaction mixture at 25-30° C. and stirred for 30 min at the same temperature. Cooled the reaction mixture to 0-5° C., acetic acid (129.1 ml) was slowly added and stirred the reaction mixture for 30 min at the same temperature. Raised the temperature of the reaction mixture to 25-30° C. and stirred for 7 hrs at the same temperature. Cooled the reaction mixture to 0-5° C. and stirred for 10 min at the same temperature. Basified the reaction mixture using aqueous sodium carbonate solution at 0-5° C. Heated the reaction mixture to 60-65° C. and stirred for 8 hrs at the same temperature. Distilled off tetrahydrofuran completely from the reaction mixture under reduced pressure. Dichloromethane was added to the reaction mixture at 25-30° C. and stirred for 10 min at the same temperature. Both the organic and aqueous layers were separated and washed the organic layer with aqueous sodium chloride solution. Distilled off the solvent completely from the organic layer and co-distilled with methyl tert.butyl ether. Methyl tert.butyl ether (100 ml) and methanol (100 ml) were added to the obtained compound at 25-30° C. and stirred the reaction mixture for 1 hr at the same temperature. Filtered the solid, washed with methyl tert.butyl ether and then dried the material to provide the title compound.

Yield: 62.0 gm; M.R: 115-120° C.

Example-2: Preparation of (S)-1-(3-ethoxy-4-methoxyphenyl)-2-(methylsulfonyl) ethanamine N-acetyl-L-leucine salt (Formula-5a)

A mixture of 1-(3-ethoxy-4-methoxyphenyl)-2-(methylsulfonyl)ethanamine compound of formula-4 (100 gm), N-acetyl-L-leucine (38 gm), methanol (400 ml) and N,N-dimethylformamide (400 ml) was heated to 55-60° C. and stirred for 7 hrs at the same temperature. Cooled the reaction mixture to 25-30° C. and stirred for 2 hrs at the same temperature. Filtered the solid, washed with methanol and spin dried the material to provide the title compound.

Yield: 85.0 gm.

Example-3: Purification of Compound of Formula-5a

Compound of formula-5a obtained in above example was added to methanol (500 ml) at 25-30° C. Heated the reaction, mixture, to 60-65° C. and stirred for 2 hrs at the same temperature. Cooled the reaction mixture to 25-30° C. and stirred for 2 hrs at the same temperature. Filtered the solid, washed with methanol and spin dried the material to provide pure title compound.

Yield: 75.0 gm.

Example-4: Preparation of (S)-1-(3-ethoxy-4-methoxyphenyl)-2-(methylsulfonyl) ethanamine (Formula-6)

(S)-1-(3-ethoxy-4-methoxyphenyl)-2-(methylsulfonyl) ethanamine N-acetyl-L-leucine salt compound of formula-5a obtained in above example and dichloromethane (450 ml) were added to water (350 ml) at 25-30° C. and stirred the reaction mixture for 10 min at the same temperature. Basified the reaction mixture using aqueous sodium carbonate solution (28 gm of sodium carbonate in 280 ml of water) at 25-30° C. and stirred the reaction mixture for 15 min at the same temperature. Both the organic and aqueous layers were separated and washed the organic layer with water. Distilled off the solvent completely from the organic layer under reduced pressure and co-distilled with methanol to provide the title compound as a solid.

Yield: 40.0 gm.

Example-5: Preparation of (S)-1-(3-ethoxy-4-methoxyphenyl)-2-(methylsulfonyl) ethanamine N-acetyl-L-leucine salt (Formula-5a)

Methanol (140 ml) and N,N-dimethylformamide (140 ml) were added to (S)-1-(3-ethoxy-4-methoxyphenyl)-2-(methylsulfonyl)ethanamine compound of formula-6 obtained in above example at 25-30° C. and stirred the reaction mixture for 10 min at the same temperature. N-Acetyl-L-leucine (25.3 gm) was added to the reaction mixture at 25-30° C. Heated the reaction mixture to 55-60° C. and stirred for 7 hrs at the same temperature. Cooled the reaction mixture to 25-30° C. and stirred for 2 hrs at the same temperature. Filtered the solid, washed with methanol and then spin dried the material. Methanol (375 ml) was added to the obtained compound at 25-30° C. Heated the reaction mixture to 60-65° C. and stirred for 2 hrs at the same temperature. Cooled the reaction mixture to 25-30° C. and stirred for 2 hrs at the same temperature. Filtered the solid, washed with methanol and then dried the material to provide the title compound.

Yield: 52.0 gm; M.R: 190-200° C.

Example-6: Preparation of N-[2-[(1S)-1-(3-ethoxy-4-methoxyphenyl)-2-(methylsulfonyl) ethyl]-2,3-dihydro-1,3-dioxo-1H-isoindol-4-yl]acetamide (Formula-1)

A mixture of N-(1,3-dioxo-1,3-dihydroisobenzofuran-4-yl)acetamide compound of formula-7 (22.9 gm), (S)-1-(3-ethoxy-4-methoxyphenyl)-2-(methylsulfonyl)ethanamine N-acetyl-L-leucine salt compound of formula-5a (50 gm) and N,N-dimethylformamide (150 ml) was heated to 85-90° C. and stirred for 7 hrs at the same temperature. Cooled the reaction mixture to 25-30° C. and quenched with aqueous sodium bicarbonate solution. Dichloromethane was added to the reaction mixture at 25-30° C. and stirred for 10 min at the same temperature. Both the organic and aqueous layers were separated and the organic layer was washed with aqueous sodium bicarbonate solution followed by with aqueous HCl solution and then finally washed with water. Distilled off the solvent completely from the organic layer and co-distilled with methanol. Methanol (150 ml) was added to the obtained compound at 25-30° C. and stirred the reaction mixture for 1 hr at the same temperature. Cooled the reaction mixture to 5-10° C. and stirred for 2 hrs at the same temperature. Filtered the solid, washed with methanol and then dried the material to provide the title compound.

Yield: 40.0 gm; M.R: 145-155° C.

Example-7: Preparation of Crystalline Form-B of Compound of Formula-1

A mixture of compound of formula-1 (75 gm) and dichloromethane (525 ml) was stirred for 20 min at 25-30° C. Filtered the reaction mixture and distilled off the solvent completely from the filtrate and then co-distilled with methanol. Methanol (225 ml) and ethyl acetate (75 ml) were added to the obtained compound at 25-30° C. and stirred the reaction mixture for 30 min at the same temperature. Heated the reaction mixture to 60-65° C. and stirred for 1 hr at the same temperature. Cooled the reaction mixture to 25-30° C. and stirred for 2 hrs at the same temperature. Filtered the solid, washed with methanol and then dried the material to provide the title compound.

Yield: 64.0 gm; M.R: 150-160° C.

Example-8: Preparation of Amorphous Form of Compound of Formula-1

A solution of compound of formula-1 (0.4 gm) in dichloromethane (2 ml) was added to n-heptane (50 ml) at 25-30° C. and stirred the reaction mixture for 5 min at the same temperature. Filtered the precipitated solid and then dried the material to provide the title compound.

Yield: 320.0 mg.

Example-9: Preparation of Amorphous Form of Compound of Formula-1

A solution of compound of formula-1 (500 mg) in acetone (6 ml) was added to pre-cooled water (40 ml) at 0-5° C. and stirred the reaction mixture for 5 min at the same temperature. Filtered the precipitated solid and then dried the material to provide the title compound.

Yield: 390.0 mg.

Example-10: Preparation of Amorphous Form of Compound of Formula-1

A solution of compound of formula-1 (500 mg) in-methanol (20 ml) was added to pre-cooled water (40 ml) at 0-5° C. and stirred the reaction mixture for 5 min at the same temperature. Filtered the precipitated solid and dried to provide the title compound.

Yield: 382.0 mg.

Example-11: Preparation of Amorphous Form of Compound of Formula-1

A solution of compound of formula-1 (500 mg) in dimethylsulfoxide (3 ml) was added to pre-cooled water (40 ml) at 0-5° C. and stirred the reaction mixture for 5 min at the same temperature. Filtered the precipitated solid and then dried the material to provide the title compound.

Yield: 350.0 mg.

Example-12: Preparation of Crystalline Form-B of Compound of Formula-1

A solution of compound of formula-1 (500 mg) in acetone (10 ml) was added to pre-heated n-heptane (50 ml) at 55-60° C. and stirred the reaction mixture for 5 min at the same temperature. Slowly cooled the reaction mixture to 25-30° C. and stirred for 1 hr at the same temperature. Filtered the precipitated solid and then dried the material to provide the title compound.

Yield: 400.0 mg.

Example-13: Preparation of Crystalline Form-B of Compound of Formula-1

A mixture of dimethylformamide and water (6 ml) in 1:1 ratio was added to compound of formula-1 (500 mg) at 25-30° C. Slowly heated the reaction mixture to 55-60° C. and stirred for 5 hrs at the same temperature. Filtered the solid and then dried the material to provide the title compound.

Yield: 410.0 mg.

Example-14: Preparation of Crystalline Form-B of Compound of Formula-1

Same as the process as exemplified in above example but instead of DMF/water mixture, a mixture of THF and water (10 ml) in 1:1 ratio has been used as solvent system.

Yield: 380.0 mg.

Example-15: Preparation of Crystalline Form-M of Compound of Formula-1

A mixture of compound of formula-1 (5 gm) and acetone (35 ml) was heated to 50-55° C. and stirred the reaction mixture for 10 min at the same temperature. The obtained solution was slowly added to pre-cooled water (500 ml) at 5-10° C. and stirred the reaction mixture for 6 hrs at the same temperature. Filtered the precipitated solid, washed with water and then dried the material to provide the title compound.

The PXRD pattern of the obtained compound is shown in FIG. 5.

Yield: 4.3 gm.

Example-16: Preparation of 3-Aminophthalic Acid Hydrochloride (Formula-11a)

3-Nitrophthalic acid compound of formula-8 (100 gm) was added to a solution of sodium bicarbonate (99.5 gm) in water (700 ml) at 25-30° C. and stirred the reaction mixture for 10 min at the same temperature. Iron powder (2.6 gm) was added to the reaction mixture at 25-30° C. and stirred for the reaction mixture for 5 min at the same temperature. Charcoal (10 gm) was added to the reaction mixture. Heated the reaction mixture to 90-95° C. 80% Hydrazine hydrate solution (59.3 ml) was slowly added to the reaction mixture at 90-95° C. and stirred for 6 hrs at the same temperature. Cooled the reaction mixture to 25-30° C. Filtered the reaction mixture through hyflow bed and washed the hyflow bed with water. Cooled the filtrate to 10-15° C., slowly acidified the reaction mixture using aqueous hydrochloric acid solution and stirred for 2 hrs at the same temperature. Filtered the precipitated solid, washed with isopropyl alcohol and then suck dried the material. Aqueous hydrochloric acid solution was added to the obtained compound at 25-30° C. and stirred the reaction mixture for 2 hrs at the same temperature. Cooled the reaction mixture to 10-15° C. and stirred for 2 hrs at the same temperature. Filtered the solid, washed with isopropyl alcohol and then dried the material to get the title compound.

Yield: 74.0 gm; M.R: 175-185° C.

Example-17: Preparation of N-(1,3-dioxo-1,3-dihydroisobenzofuran-4-yl)acetamide (Formula-7)

A mixture of 3-aminophthalic acid hydrochloride compound of formula-11a (50 gm) and acetic anhydride (150 ml) was heated to 115-120° C. and stirred the reaction mixture for 4 hrs at the same temperature. Slowly cooled the reaction mixture to 0-5° C. and stirred for 2 hrs at the same temperature. Filtered the precipitated solid, washed with methyl tert.butyl ether and then dried the material to get the title compound.

Yield: 40.0 gm; M.R: 175-180° C.

Example-18: Preparation of 1-(3-ethoxy-4-methoxyphenyl)-2-(methylsulfonyl)ethanamine (Formula-4)

3M methyl magnesium chloride solution in tetrahydrofuran (141 ml) was slowly added to a pre-cooled mixture of dimethylsulfone (26.5 gm) and tetrahydrofuran (250 ml) at 0-5° C. under nitrogen atmosphere and stirred the reaction mixture for 1 hr at the same temperature. A solution of 3-ethoxy-4-methoxybenzonitrile compound of formula-2 (25 gm) in tetrahydrofuran (125 ml) was slowly added to the reaction mixture at 0-5° C. and stirred the reaction mixture for 15 min at the same temperature. Heated the reaction mixture to 40-45° C. and stirred for 4 hrs at the same temperature. Cooled the reaction mixture to 25-30° and NaBH$_4$ (13.5 gm) was slowly added to it. Further cooled the reaction mixture to 0-5° C. and stirred for 15 min at the same temperature. Acetic acid (48.5 ml) was slowly added to the reaction mixture at 0-5° C. and stirred the reaction mixture for 5 hrs at the same temperature. Aqueous sodium hydroxide solution was slowly added to the reaction mixture at 0-5° C. and stirred for 30 min at the same temperature. Heated the reaction mixture to 60-65° C. and stirred for 12 hrs at the same temperature. Cooled the reaction mixture to 25-30° C. Dichloromethane and water were added to the reaction mixture at 25-30° C. and stirred for 15 min at the same temperature. Both the organic and aqueous layers were separated and washed the organic layer with aq.NaCl solution and dried over sodium sulfate. Distilled off the solvent from the organic layer and co-distilled with methyl tert.butyl ether. 125 ml of methyl tert.butyl ether was added to the obtained compound at 25-30° C. and stirred the reaction mixture for 90 min at the same temperature. Filtered the solid, washed with methyl tert.butyl ether and dried to get the title compound.

Yield: 29.0 gm.

Example-19: Preparation of 1-(3-ethoxy-4-methoxyphenyl)-2-(methylsulfonyl)ethanamine (Formula-4)

3M methyl magnesium chloride solution in tetrahydrofuran (117.5 ml) was slowly added to a pre-cooled mixture of dimethylsulfone (26.5 gm), 3-ethoxy-4-methoxybenzonitrile compound of formula-2 (25 gm) and tetrahydrofuran (250 ml) at 0-5° C. under nitrogen atmosphere. Raised the temperature of the reaction mixture to 25-30° C. and stirred for 5 hrs at the same temperature. Sodium borohydride (8 gm) was slowly added to the reaction mixture at 25-30° C. Cooled the reaction mixture to 0-5° C. and stirred for 15 min at the same temperature. Acetic acid (64.5 ml) was slowly added to the reaction mixture at 0-5° C. Heated the reaction mixture to 40-45° C. and stirred for 5 hrs at the same temperature. Cooled the reaction mixture to 0-5° C. and stirred for 15 min at the same temperature. Slowly added aqueous sodium hydroxide solution to the reaction mixture at 0-5° C. and stirred for 30 min at the same temperature. Heated the reaction mixture to 60-65° C. and stirred for 12 hrs at the same temperature. Cooled the reaction mixture to 25-30° C., dichloromethane and water were added and stirred the reaction mixture for 15 min. Both the organic and aqueous layers were separated and washed the organic layer with aqueous sodiuim chloride solution. Distilled off the solvent completely from the organic layer and co-distilled with methyl tert.butyl ether. 125 ml of methyl tert.butyl ether was added to the obtained compound at 25-30° C. and stirred the reaction mixture for 90 min at the same temperature. Filtered the solid, washed with methyl tert butyl ether and then dried the material to get the title compound.

Yield: 29.0 gm.

Example-20: Preparation of 1-(3-ethoxy-4-methoxyphenyl)-2-(methylsulfonyl)ethanamine (Formula-4)

A mixture of dimethylsulfone (26.5 gm) and dimethylsulfoxide (250 ml) was stirred for 15 min at 25-30° C. under nitrogen atmosphere. Potassium tert.butoxide (39.5 gm) was added to the reaction mixture at 25-30° C. Heated the reaction mixture to 40-45° C. and stirred for 2 hrs at the same temperature. Cooled the reaction mixture to 25-30° C. A solution of 3-ethoxy-4-methoxybenzonitrile compound of formula-2 (25 gm) in dimethylsulfoxide (250 ml) was slowly added to the reaction mixture at 25-30° C. and stirred for 6 hrs at the same temperature. Cooled the reaction mixture to 0-5° C., sodium borohydride (13.9 gm) was slowly added to it and stirred the reaction mixture for 20 min at the same temperature. Acetic acid (49 ml) was slowly added to the reaction mixture at 0-5° C. and stirred the reaction mixture for 10 hrs at the same temperature. Aqueous sodium hydroxide solution was slowly added to the reaction mixture at 0-5° C. Heated the reaction mixture to 60-65° C. and stirred for 1 hr at the same temperature. Cooled the reaction mixture to 25-30° C., water and dichloromethane were added and stirred the reaction mixture for 15 min. Both the organic and aqueous layers were separated and washed the organic layer with aqueous sodium chloride solution. Distilled off the solvent completely from the organic layer and co-distilled with methyl tert.butyl ether. 100 ml of methyl tert.butyl ether was added to the obtained compound at 25-30° C. and stirred for 1 hr at the same temperature. Filtered the reaction mixture, washed the compound with methyl tert.butyl ether and then dried the material to get the title compound.

Yield: 30.0 gm.

Example-21: Preparation of (S)-1-(3-ethoxy-4-methoxyphenyl)-2-(methylsulfonyl) ethanamine N-acetyl-L-leucine salt (Formula-5a)

A mixture of 1-(3-ethoxy-4-methoxyphenyl)-2-(methylsulfonyl)ethanamine compound of formula-4 (5 gm), N-acetyl-L-leucine (1.9 gm) and, methanol (35 ml) was heated to 45-50° C. and stirred the reaction mixture for 1 hr at the same temperature. Cooled the reaction mixture to 25-30° C. and stirred for 3 hrs at the same temperature. Filtered the precipitated solid, washed with methanol and then dried the material to get the title compound.

Yield: 3.5 gm.

Example-22: Purification of Compound of Formula-5a

A mixture of compound of formula-5a (3 gm) and methanol (24 ml) was heated to 60-65° C. and stirred the reaction mixture for 1 hr at the same temperature. Cooled the reaction mixture to 25-30° C. and stirred for 3 hrs at the same temperature. Filtered the solid, washed with methanol and then dried the material to get the pure title compound.

Yield: 2.0 gm.

Example-23: Preparation of Compound of Formula-1

A mixture of (S)-1-(3-ethoxy-4-methoxyphenyl)-2-(methylsulfonyl)ethanamine N-acetyl-L-leucine salt compound of formula-5a (50 gm), N-(1,3-dioxo-1,3-dihydro isobenzofuran-4-yl)acetamide compound of formula-7 (24 gm) and acetic acid (500 ml) was heated to 95-100° C. and stirred the reaction mixture for 7 hrs at the same temperature. Reduced the temperature of the reaction mixture to 60-65° C. and distilled off the solvent completely under reduced pressure. Cooled the reaction mixture to 25-30° C. Ethyl acetate followed by water were added to the reaction mixture and stirred for 5 min. Both the organic and aqueous layers were separated and washed the organic layer with aqueous sodium bicarbonate solution followed by with aqueous sodium chloride solution. Dried the organic layer over sodium sulfate and distilled off the solvent completely under reduced pressure. Methanol (150 ml) was added to the obtained compound at 25-30° C. and stirred the reaction mixture for 2 hrs at the same temperature. Filtered the solid, washed with methanol and then dried the material to get the title compound.

Yield: 40.0 gm.

Example-24: Preparation of Crystalline Form-B of Compound of Formula-1

A mixture of compound of formula-1 (45 gm), methanol, (135 ml) and acetone (45 ml) was heated to 50-55° C. and stirred the reaction mixture for 90 min at the same temperature. Cooled the reaction mixture to 25-30° C. and stirred for 3 hrs at the same temperature. Filtered the precipitated solid, washed with methanol and then dried the material to get the title compound.

Yield: 36.0 gm.

Example-25: Preparation of Amorphous Form of Compound of Formula-1 Using Acetone A mixture of compound of formula-1 (5 gm) and acetone (75 ml) was stirred for 20 min at 25-30° C. Distilled off the solvent completely from the reaction mixture under reduced pressure and then dried the material to get the title compound.

Figure 6:
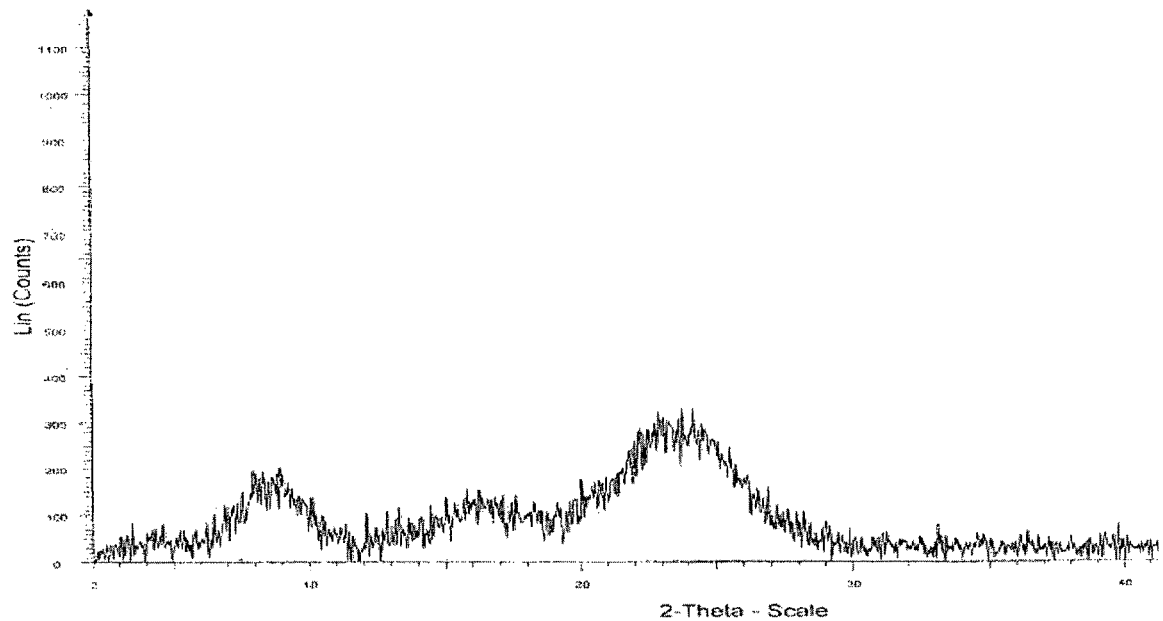
FIG. 6: Illustrates the PXRD pattern of compound of formula-1 obtained according to example-25.

The PXRD pattern of the obtained compound is shown in FIG. 6.

Yield: 4.7 gm.

Example-26: Preparation of Amorphous Form of Compound of Formula-1 Using Dichloromethane A mixture of compound of formula-1 (5 gm) and dichloromethane (60 ml) was stirred for 20 min at 25-30° C. Distilled off the solvent completely from the reaction mixture under reduced pressure and then dried the material to get the title compound.

Figure 7:
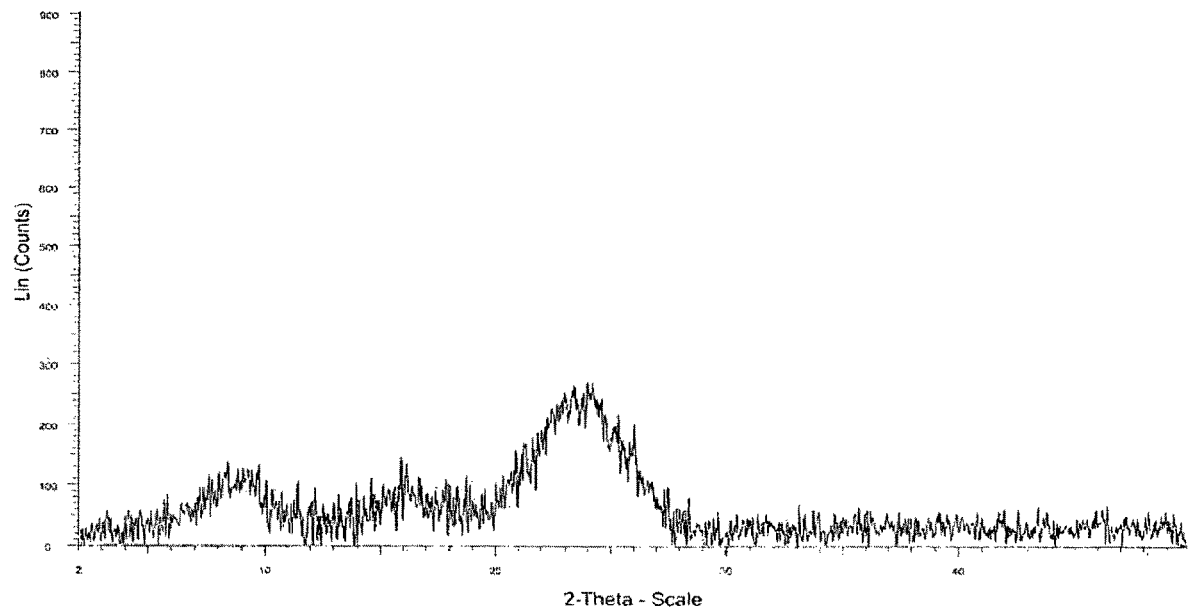
FIG. 7: Illustrates the PXRD pattern of compound of formula-1 obtained according to example-26.

The PXRD pattern of the obtained compound is shown in FIG. 7.

Yield: 4.5 gm.

Example-27: Preparation of Amorphous Form of Compound of Formula-1 Using Mixture of Dichloromethane and Acetone A mixture of compound of formula-1 (5 gm), dichloromethane (15 ml) and acetone (15 ml) was stirred for 20 min at 25-30° C. Distilled off the solvent completely from the reaction mixture under reduced pressure and then dried the material to get the title compound.

Figure 8:
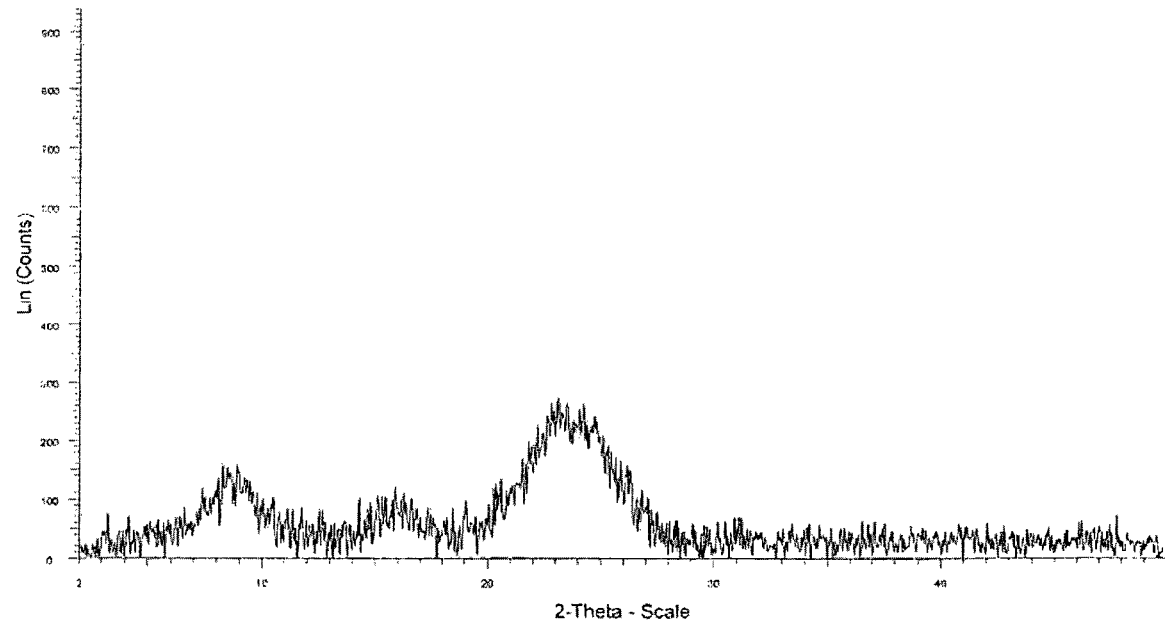
FIG. 8: Illustrates the PXRD pattern of compound of formula-1 obtained according to example-27.

The PXRD pattern of the obtained compound is shown in FIG. 8.

Yield: 4.6 gm.

Example-28; Preparation of amorphous form of compound of formula-1 using acetone A mixture of compound of formula-1 (3; gm) and acetone (40 ml) was stirred for 20 min at 25-30° C. Distilled off the solvent completely from the reaction mixture under reduced pressure. n-Heptane (15 ml) was added to the obtained compound at 25-30° C. and stirred the reaction mixture for 1 hr at the same temperature. Filtered the solid and then dried to get the title compound.

Figure 9:
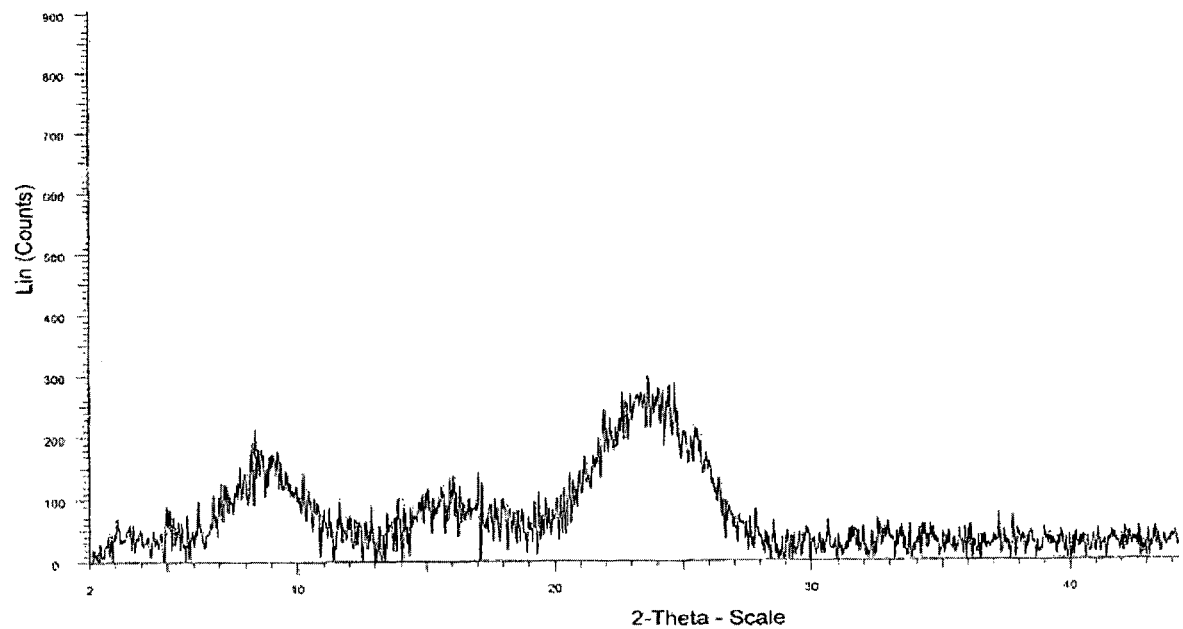
FIG. 9: Illustrates the PXRD pattern of compound of formula-1 obtained according to example-28.

The PXRD pattern of the obtained compound is shown in FIG. 9.

Yield: 2.3 gm.

Example-29: Preparation of Compound of Formula-1 Using Mixture of Acetone and Ethyl Acetate A mixture of compound of formula-1 (3 gm); acetone (21 ml) and ethyl acetate (9 ml) was stirred for 20 min at 25-30° C. Distilled off the solvent completely from the reaction mixture under reduced pressure and then dried the material to get the title compound.

Figure 10:
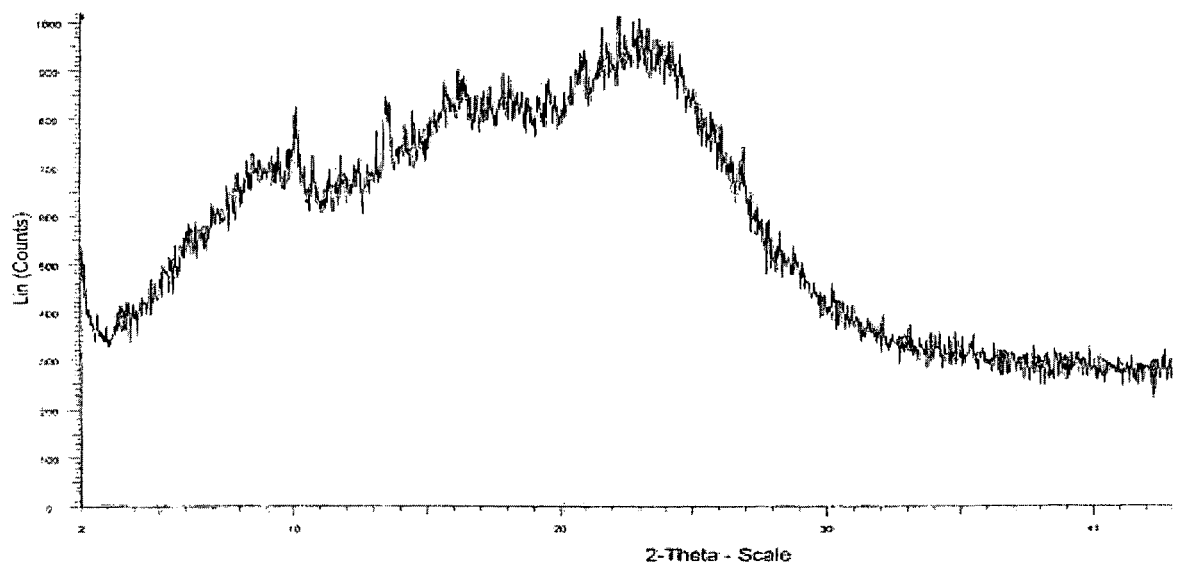
FIG. 10: Illustrates the PXRD pattern of compound of formula-1 obtained according to example-29.

The PXRD pattern of the obtained compound is shown in FIG. 10.

Yield: 2.8 gm.

Example-30: Preparation of Amorphous Form of Compound of Formula-1

A mixture of compound of formula-1 (75 gm) and acetone (375 ml) was heated to 45-50° C. and stirred for 15 min at the same temperature. Cooled the reaction mixture to 25-30° C. Filtered the solution through hyflow bed to make it particle free and washed the hyflow bed with acetone. Cooled the filtrate to 20-25° C. and was slowly added to a pre-cooled mixture of water (1220 ml) and acetone (75 ml) at 0-5° C. and stirred for 30 min at the same temperature. Filtered the precipitated solid, washed with water and dried the material to get the title compound.

Yield: 65.0 gm.

Example-31: Preparation of Amorphous Form of Compound of Formula-1

A mixture of compound of formula-1 (75 gm), methanol (225 ml) and ethyl acetate (75 ml) was heated to 60-65° C. and stirred the reaction mixture for 1 hr at the same temperature. Cooled the reaction mixture to, 25-30° C. and stirred for 2 hrs at the same temperature. Filtered the solid, washed with methanol and suck dried the material. The obtained solid was added to acetonitrile (262.5 ml) at 25-30° C. Heated the reaction mixture to 60-65° C. and stirred for 15 min at the same temperature. Cooled the reaction mixture to 25-30° C. Filtered the reaction mixture through hyflow bed to make it particle free and washed the hyflow bed with acetonitrile. The obtained filtrate was added to pre-cooled water (3750 ml) at 10-15° C. and stirred for 1 hr at the same temperature. Filtered the precipitated solid, washed with chilled water and dried the material to get the title compound.

Yield: 54.0 gm.

Example-32: Preparation of Amorphous Form of Compound of Formula-1

A mixture of compound of formula-1 (75 gm) and dichloromethane (525 ml) was stirred for 20 min at 25-30° C. Filtered the reaction mixture to make it particle free. Distilled off the solvent from the filtrate. 1,4-dioxane (112.5 ml) was added to the obtained compound at 25-30° C. and stirred the reaction mixture for 15 min at the same temperature. The obtained solution was added to pre-cooled water (7500 ml) at 10-15° C. and stirred the reaction mixture for 30 min at the same temperature. Filtered the precipitated solid, washed with water and dried the material to get the title compound.

Yield: 65.0 gm.

Example-33: Preparation of 1-(3-ethoxy-4-methoxyphenyl)-2-(methylsulfonyl) ethanamine (Formula-4)

3M Methyl magnesium chloride solution in tetrahydrofuran (235.15 Lt) was slowly added to a pre-cooled mixture of 3-ethoxy-4-methoxybenzonitrile compound of formula-2 (50 Kg), dimethyl sulfone (53.12 Kg) and tetrahydrofuran (500 Lt) at 0-5° C. under nitrogen atmosphere. Raised the temperature of the reaction mixture to 25-30° C. and stirred for 6 hrs at the same temperature. Sodium borohydride (21.5 Kg) was added to the reaction mixture at 25-30° C. and stirred for 30 min at the same temperature. Cooled the reaction mixture to 0-5° C., acetic acid (129 Lt) was slowly added and stirred for 45 min at the same temperature. Raised the temperature of the reaction mixture to 25-30° C. and stirred for 7 hrs at the same temperate. Cooled the reaction mixture to 0-5° C. and stirred for 10 min at the same temperature; Water was slowly added to the reaction mixture at 0-5° C. and basified the reaction mixture using aqueous sodium carbonate solution. Heated the reaction mixture to 60-65° C. and stirred for 8 hrs at the same temperature. Distilled off tetrahydrofuran completely from the reaction mixture under reduced pressure. Cooled the reaction mixture to 25-30° C. Dichloromethane was added to the reaction mixture at 25-30° C. and stirred for 15 min at the same temperature. Both the organic and aqueous layers were separated and washed the organic layer with aqueous sodium chloride solution. Distilled off the solvent completely from the organic layer and co-distilled with methyl tert.butyl ether under reduced pressure. Methyl tert.butyl ether (100 Lt) and methanol (100 Lt) were added to the obtained compound at 25-30° C. and stirred the reaction mixture for 90 min at the same temperature. Filtered the solid, washed with methyl tert.butyl ether and dried the material to provide the title compound.

Yield: 55.3 Kg; Purity by HPLC: 99.5%.

Imine impurity: Not detected; Benzaldehyde impurity: Not detected; Benzonitrile impurity: Not detected.

Example-34: Preparation of (S)-1-(3-ethoxy-4-methoxyphenyl)-2-(methylsulfonyl) ethanamine N-acetyl-L-leucine salt (Formula-5a)

N-acetyl-L-leucine (19 Kg) was added to a mixture of 1-(3-ethoxy-4-methoxy phenyl)-2-(methylsulfonyl)ethanamine compound of formula-4 (50 Kg), methanol (200 Lt) and Dimethyl formamide (200 Lt) at 25-30° C. Heated the reaction mixture to 55-60° C. and stirred for 7 hrs at the same temperature. Cooled the reaction mixture to 25-30° C. and stirred for 2 hrs at the same temperature. Filtered the solid, washed with methanol and spin dried the material. The obtained solid was added to water (175 Lt) at 25-30° C. Dichloromethane (225 Lt) was added to the reaction mixture at 25-30° C. and stirred for 15 min at the same temperature. Basified the reaction mixture using aqueous sodium carbonate solution at 25-30° C. and stirred for 15 min at the same temperature. Both the organic and aqueous layers were separated and washed the organic layer with water. Distilled off the solvent completely from the organic layer and co-distilled with methanol. Dimethylformamide (85 Lt) and methanol (85 Lt) were added to the obtained compound at 25-30° C. and stirred for 15 min at the same temperature. N-Acetyl-L-leucine (12.7 Kg) was added to the reaction mixture at 25-30° C. Heated the reaction mixture to 55-60° C. and stirred for 7 hrs at the same temperature. Cooled the reaction mixture to 25-30° C. and stirred for 2 hrs at the same temperature. Filtered the solid, washed with methanol and spin dried the material. The obtained solid was added to water (150 Lt) at 25-30° C. Dichloromethane (200 Lt) was added to the reaction mixture at 25-30° C. and stirred for 15 min at the same temperature. Basified the reaction mixture using aqueous sodium carbonate solution at 25-30° C. and stirred for 15 min at the same temperature. Both the organic and aqueous layers were separated and washed the organic layer with water. Distilled off the solvent completely from the organic layer and co-distilled with methanol. Dimethylformamide (75 Lt) and methanol (75 Lt) were added to the obtained compound at 25-30° C. and stirred for 15 min at the same temperature. N-Acetyl-L-leucine (11.1 Kg) was added to the reaction mixture at 25-30° C. Heated the reaction mixture to 55-60° C. and stirred for 7 hrs at the same temperature. Cooled the reaction mixture to 25-30° C. and stirred for 2 hrs at the same temperature. Filtered the solid, washed with methanol and spin dried the material. Methanol (125 Lt) was added to the obtained solid at 25-30° C. Heated the reaction mixture to 60-65° C. and stirred for 2 hrs at the same temperature. Cooled the reaction mixture to 25-30° C. and stirred for 2 hrs at the same temperature. Filtered the solid, washed with methanol and dried the material to get the title compound.

Yield: 20.6 Kg; Purity by HPLC: 99.98%.

Imine impurity: Not detected; Benzonitrile impurity: Not detected; (R)-isomer impurity: 0.05%.

Example-35: Preparation of 3-Aminophthalic Acid Hydrochloride (Formula-11a)

3-Nitrophthalic acid compound of formula-8 (25 Kg) was added to a solution of sodium bicarbonate (24.75 Kg) in water (175 Lt) at 25-30° C. and stirred the reaction mixture for 15 min at the same temperature. Iron powder (0.65 Kg) and charcoal (2.5 Kg) were added to the reaction mixture at 25-30° C. Heated the reaction mixture to 95-100° C. 80% Hydrazine hydrate solution (14.75 Lt) was slowly added to the reaction mixture at 90-95° C. and stirred for 6 hrs at the same temperature. Cooled the reaction mixture to 25-30° C. Filtered the reaction mixture through hyflow bed and washed the hyflow bed with water. Cooled the filtrate to 10-15° C., slowly acidified the reaction mixture using aqueous hydrochloric acid solution and stirred for 3 hrs at the same temperature. Filtered the precipitated solid, washed with isopropyl alcohol and dried the material. Aqueous hydrochloric acid solution was added to the obtained compound at 25-30° C. and stirred the reaction mixture for 90 min at the same temperature. Cooled the reaction mixture to 10-15° C. and stirred for 90 min at the same temperature. Filtered the solid, washed with isopropyl alcohol and then dried the material to get the title compound.

Yield: 16.5 Kg.

Example-36: Preparation of N-(1,3-dioxo-1,3-dihydroisobenzofuran-4-yl)acetamide (Formula-7)

A mixture of 3-aminophthalic acid hydrochloride compound of formula-11a (16 Kg) and acetic anhydride (52.18 Kg) was stirred for 10 min at 25-30° C. Heated the reaction mixture to 85-90° C. and stirred for 4 hrs at the same temperature. Slowly cooled the reaction mixture to 0-5° C. and stirred for 3 hrs at the same temperature. Filtered the precipitated solid, washed with methyl tert.butyl ether and then dried the material to get the title compound.

Yield: 12.1 Kg.

Example-37: Preparation of Compound of Formula-1

A mixture of (S)-1-(3-ethoxy-4-methoxyphenyl)-2-(methylsulfonyl)ethanamine N-acetyl-L-leucine salt compound of formula-5a (20 Kg) and dimethylformamide (60 Lt) was stirred for 10 min at 25-30° C. N-(1,3-dioxo-1,3-dihydroisobenzofuran-4-yl)acetamide compound of formula-7 (9.2 Kg) was added to the reaction mixture at 25-30° C. Heated the reaction mixture to 85-90° C. and stirred for 6 hrs at the same temperature. Cooled the reaction mixture to 25-30° C. and aqueous sodium bicarbonate solution was added to it. Dichloromethane was added to the reaction mixture at 25-30° C. and stirred for 15 min at the same temperature. Both the organic and aqueous layers were separated and washed the organic layer with aqueous sodium bicarbonate solution followed by with aqueous hydrochloric acid and then with water. Distilled off the solvent completely from the organic layer and co-distilled with methanol under reduced pressure. Methanol (60 Lt) was added to the obtained compound at 25-30° C. and stirred for 5 hrs at the same temperature. Filtered the solid, washed with methanol and dried the material to provide the title compound.

Yield: 16.3 Kg; Purity by HPLC: 99.89%.

Example-38: Preparation of Crystalline Form-B of Compound of Formula-1

A mixture of compound of formula-1 (15 Kg) and dichloromethane (105 Lt) was stirred for 20 min at 25-30° C. Filtered the reaction mixture, distilled off the solvent completely from the filtrate and co-distilled with methanol under reduced pressure. Methanol (45 Lt) and ethyl acetate (0.1.5 Lt) were added to the obtained compound at 25-30° C. and stirred for 30 min at the same temperature. Heated the reaction mixture to 60-65° C. and stirred for 1 hr at the same temperature. Cooled the reaction mixture to 25-30° C. and stirred for 2 hrs at the same temperature. Filtered the solid, washed with methanol and then dried the material to get the title compound.

Yield: 11.4 Kg; Purity by HPLC: 99.93%.

Water content by KFR: 0.23% w/w.

Particle size distribution: D(0.1) is 2530 μm; D(0.5) is 6.63 μm; D(0.9) is 19.8 μm.

Example-39: Preparation of Crystalline Form-B of Compound of Formula-1

A mixture of (S)-1-(3-ethoxy-4-methoxyphenyl)-2-(methylsulfonyl)ethanamine N-acetyl-L-leucine salt compound of formula-5a (50 gm), N-(1,3-dioxo-1,3-dihydroisobenzofuran-4-yl)acetamide compound of formula-7 (22.97 gm) and dimethylformamide (150 ml) was heated to 85-90° C. and stirred for 7 hrs at the same temperature. Cooled the reaction mixture to 25-30° C. and aqueous sodium bicarbonate solution was added to it. Dichloromethane was added to the reaction mixture at 25-30° C. and stirred for 10 min at the same temperature. Both the organic and aqueous layers were separated and washed the organic layer with aqueous sodium bicarbonate solution followed by with aqueous hydrochloric acid and then with water. Distilled off the solvent completely from the organic layer and cooled the reaction mixture to 25-30° C. Acetone (50 ml) and ethanol (100 ml) were added to the reaction mixture at 25-30° C. and stirred the reaction mixture for 1 hr at the same temperature. Further cooled the reaction mixture to 5-10° C. and stirred for 2½ hrs at the same temperature. Filtered the solid, washed with ethanol and dried the material to get the title compound.

Yield: 40.0 gm.

Example-40: Preparation of Crystalline Form-B of Compound of Formula-1

A mixture of compound of formula-1 (75 gm) and dichloromethane (525 ml) was stirred for 20 min at 25-30° C. Filtered the reaction mixture to make it particle free. Distilled off the solvent from the filtrate and co-distilled with ethanol. 150 ml of ethanol and 75 ml of acetone were added to the obtained compound at 25-30° C. and stirred for 30 min at the same temperature. Heated the reaction mixture to 60-65° C. and stirred for 1 hr at the same temperature. Cooled the reaction mixture to 25-30° C. and stirred for 2 hrs at the same temperature. Filtered the solid, washed with ethanol and dried the material to get the title compound.

Yield: 62.5 gm.

Example-41: Preparation of Compound of Formula-1

A mixture of (S)-1-(3-ethoxy-4-methoxyphenyl)-2-(methylsulfonyl)ethanamine N-acetyl-L-leucine salt compound of formula-5a (5 Kg), N-(1,3-dioxo-1,3-dihydroisobenzofuran-4-yl)acetamide compound of formula-7 (2.3 Kg) and dimethylformamide (15 Lt) was stirred for 15 min at 25-30° C. Heated the reaction mixture to 85-90° C. and stirred for 7 hrs at the same temperature. Cooled the reaction mixture to 25-30° C. and aqueous sodium bicarbonate solution was added to it. Dichloromethane was added to the reaction mixture at 25-30° C. and stirred for 10 min at the same temperature. Both the organic and aqueous layers were separated and washed the organic layer with aqueous sodium bicarbonate solution followed by with aqueous hydrochloric acid and then with water. Distilled off the solvent completely from the organic layer and co-distilled with acetone. Cooled the obtained compound to 25-30° C., acetone (25 Lt) was added to it and stirred the reaction mixture for 10 min at the same temperature. Slowly added the obtained solution to pre-cooled water (125 Lt) at 5-10° C. and stirred the reaction mixture for 3½ hrs at the same temperature. Filtered the precipitated solid, washed with chilled water and dried the material to get the title compound.

Yield: 4.7 Kg.

Example-42: Preparation of Crystalline Form-M of Compound of Formula-1

A mixture of compound of formula-1 (4.5 Kg), methanol (14 Lt) and ethyl acetate (5 Lt) was stirred for 10 min at 25-30° C. Heated the reaction mixture to 60-65° C. and stirred for 1 hr at the same temperature. Cooled the reaction mixture to 25-30° C. and stirred for 2 hrs at the same temperature. Filtered the solid, washed with methanol and spin dried the material. The obtained solid was added to acetone (23 Lt) at 25-30° C. Heated the reaction mixture to 45-50° C. and stirred for 15 min at the same temperature. Cooled the reaction mixture to 25-30° C. and filtered it through hyflow bed to make it particle free. Slowly added the filtrate to pre-cooled water (135 Lt) at 5-10° C. and stirred the reaction mixture for 3½ hrs at the same temperature. Filtered the precipitated solid, washed with water and dried the material to get the title compound.

Yield: 3.2 Kg; Purity by HPLC: 99.96%.

Particle Size Distribution:

D(0.1) is 2.50 μm; D(0.5) is 6.63 μm; D(0.9) is 19.8 μm.

We claim:

1. A crystalline polymorph of N-[2-[(1S)-1-(3-ethoxy-4-methoxyphenyl)-2-(methylsulfonyl)ethyl]-2,3-dihydro-1,3-dioxo-1H-isoindol-4-yl]acetamide of compound of formula-1

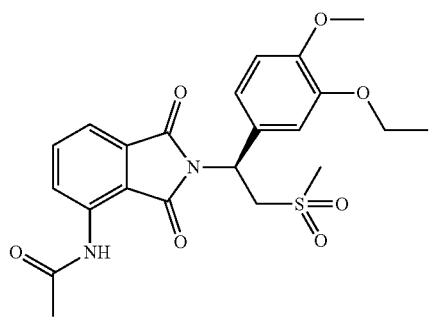

Formula-1 characterized by:
(i) its powder X-ray diffraction (PXRD) pattern having peaks at 5.4, 7.5, 8.5, 9.9, 14.1, 14.9, 16.7, 16.9, 17.7, 19.7, 21.6, 22.5, 22.8, 24.0, 25.5, 27.2 and 28.9±0.2° of 2-theta, and
(ii) a powder X-ray diffraction (PXRD) pattern as shown in FIG. 5.

2. A pharmaceutical composition comprising the crystalline polymorph of N-[2-[(1S)-1-(3-ethoxy-4-methoxyphenyl)-2-(methyl sulfonyl)ethyl]-2,3-dihydro-1,3-dioxo-1H-isoindol-4-yl]acetamide of claim 1 and at least one pharmaceutically acceptable excipient.

3. A process for the preparation of crystalline polymorph of compound of formula-1 according to claim 1, comprising:
a) dissolving the compound of formula-1 in a first solvent,
b) optionally filtering the mixture, and
c) combining the solution obtained in step a) or step b) with a second solvent; to obtain the crystalline polymorph of compound of formula-1.

4. The process according to claim 3, wherein,
the first solvent in step a) is selected from ketone solvents; and the dissolution of compound of formula-1 in a first solvent is carried out at a temperature ranging between 10° C. to reflux temperature of the first solvent;
the second solvent in step c) is a polar solvent; and combining the solution of step a) or step b) with a second solvent is carried out at a temperature ranging from 0° C. to reflux temperature of the second solvent.

5. A process for the preparation of crystalline polymorph of compound of formula-1 according to claim 1, comprising:
a) dissolving the compound of formula-1 in acetone,
b) optionally filtering the solution, and
c) combining the solution with water; to obtain the crystalline polymorph of compound of formula-1.

6. The process according to claim 5, wherein
the dissolution of the compound of formula-1 in acetone in step a) is carried out at a temperature of 50° C.-55° C.; and
the solution in step c) is slowly added to pre-cooled water at 5° C.-10° C.

* * * * *